(12) United States Patent
Xiao et al.

(10) Patent No.: US 7,498,438 B2
(45) Date of Patent: Mar. 3, 2009

(54) FUSED RING $NK_1$ ANTAGONISTS

(75) Inventors: Dong Xiao, Warren, NJ (US); Anandan Palani, Bridgewater, NJ (US); Cheng Wang, King of Prussia, PA (US); Hon-Chung Tsui, East Brunswick, NJ (US); Neng-Yang Shih, Warren, NJ (US); Gregory A. Reichard, Ann Arbor, MI (US)

(73) Assignee: Schering Corporation, Kenilworth, NJ (US)

( * ) Notice: Subject to any disclaimer, the term of this patent is extended or adjusted under 35 U.S.C. 154(b) by 394 days.

(21) Appl. No.: 11/100,226

(22) Filed: Apr. 6, 2005

(65) Prior Publication Data

US 2006/0040975 A1 Feb. 23, 2006

Related U.S. Application Data

(60) Provisional application No. 60/560,343, filed on Apr. 7, 2004.

(51) Int. Cl.
  *C07D 471/02* (2006.01)
  *C07D 491/02* (2006.01)
(52) U.S. Cl. ........................ 546/116; 546/118
(58) Field of Classification Search ............. 546/116, 546/118
  See application file for complete search history.

(56) References Cited

U.S. PATENT DOCUMENTS

| 5,102,667 A | 4/1992 | Dubroeucq et al. |
| 2002/0022624 A1 | 2/2002 | Dinnell et al. |

FOREIGN PATENT DOCUMENTS

| EP | 0429366 A | 5/1991 |
| WO | WO 00/39114 A | 7/2000 |

OTHER PUBLICATIONS

International Search Report for PCT/US2005/011726 (CN06126US01)—4 pages.

*Primary Examiner*—D. Margaret Seaman
*Assistant Examiner*—Nizal S Chandrakumar
(74) *Attorney, Agent, or Firm*—Thomas A. Blinka; Serena Farquharson-Torres; Gerard E. Reinhardt

(57) ABSTRACT

A compound having the general structure shown in Formula 1:

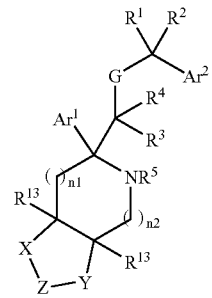

Formula 1 or pharmaceutically acceptable salts and/or solvates thereof are useful in treating diseases or conditions mediated by $NK_1$ receptors, for example various physiological disorders, symptoms or diseases, including emesis, depression, anxiety and cough.

24 Claims, No Drawings

FUSED RING NK₁ ANTAGONISTS

CROSS-REFERENCE TO RELATED APPLICATION

This application claims the benefit of priority from U.S. Provisional Patent Application Ser. No. 60/560,343, filed Apr. 7, 2003.

FIELD OF THE INVENTION

The present invention relates to novel neurokinin-1 ($NK_1$ or NK-1) receptor antagonists, pharmaceutical compositions comprising such compounds, and methods of treatment using such compounds, to treat $NK_1$ receptor mediated diseases and conditions, including, for example, emesis, depression, anxiety and cough.

BACKGROUND OF THE INVENTION

Tachykinins are peptide ligands for neurokinin receptors. Neurokinin receptors, such as $NK_1$, $NK_2$ and $NK_3$, are involved in a variety of biological processes. They can be found in a mammal's nervous and circulatory systems, as well as in peripheral tissues. Consequently, the modulation of these types of receptors has been studied to potentially treat or prevent various mammalian disease states. For instance, $NK_1$ receptors have been reported to be involved in microvascular leakage and mucus secretion. Representative types of neurokinin receptor antagonists and the disorders that can be treated with them include, for example, sleep, pain, migraine, emesis, nociception and inflammation; see, for example, U.S. Pat. No. 6,329,401, U.S. Pat. No. 5,760,018, U.S. Pat. No. 5,620,989, WO 95/19344, WO 94/13639, WO 94/10165, Wu et al., *Tetrahedron*, 56, 6279-6290 (2000), Rombouts et al., *Tetrahedron*, 59, 4721-4731 (2003), and Rogiers et al., *Tetrahedron*, 57, 8971-8981 (2001).

It would be beneficial to provide a $NK_1$ antagonist that is potent, selective, and possesses beneficial therapeutic and pharmacological properties, and good metabolic stability. It would further be beneficial to provide a $NK_1$ antagonist that is effective for treating a variety of physiological disorders, symptoms and diseases, while minimizing side effects. This invention provides such $NK_1$ antagonists.

SUMMARY OF THE INVENTION

In one embodiment, the present invention is directed to a compound of Formula 1:

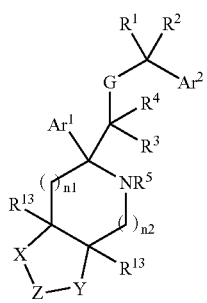

Formula 1 or a pharmaceutically acceptable salt and/or or solvate thereof, $Ar^1$ and $Ar^2$ are each independently selected from the group consisting of $(R^7)_{n7}$-aryl- and $(R^8)_{n8}$-heteroaryl-;

G is selected from the group consisting of —O—, —S—, —S(O)—, —S(O$_2$)—, —N($R^6$)—, —N(C(O)$R^6$)—, —N(S(O$_2$)$R^6$)—, —N(S(O)$R^6$)—, —N(C(O)O$R^6$)—, —N(C(O)N($R^6$)$_2$)—, —N($R^6$)S(O$_2$)—, —S(O$_2$)N($R^6$)—, —N($R^6$)SO—, —S(O)N($R^6$)—, —N($R^6$)C(O)O—, —OC(O)N($R^6$)—, —N($R^6$)C(O)—, —C(O)N($R^6$)—, and —N($R^6$)C(O)N($R^6$)—;

X is —(C($R^6$)$_2$)$_{n3}$-A-(C($R^6$)$_2$)$_{n4}$—, wherein n3 and n4 can be the same or different;

Y is —(C($R^6$)$_2$)$_{n5}$-B-(C($R^6$)$_2$)$_{n6}$—, wherein n5 and n6 can be the same or different;

A is selected from the group consisting of —O—, —S—, —C($R^6$)$_2$—, and —N($R^{14}$)—;

B is selected from the group consisting of —O—, —S—, —C($R^6$)$_2$—, and —N($R^{14}$)—;

n1, n2, n3, n4, n5, n6, and n8 are each independently an integer of from 0 to 3;

n7 is an integer of from 0 to 5;

n8 is an integer of from 1 to 3;

n9 is an integer of from 0 to 2;

n10 is an integer of from 1 to 5

Z is selected from the group consisting of —C(O)—, —C(S)—, —S(O)—, —S(O$_2$)—, —C(=N$R^6$)—, —C(=NO$R^6$)—, and —C(=NN($R^6$)$_2$)—;

$R^1$ and $R^2$ are independently selected from the group consisting of H, alkyl, hydroxyalkyl, cycloalkyl, —CH$_2$F, —CHF$_2$, —CF$_3$, and heterocycloalkyl, wherein each of said alkyl, cycloalkyl, or heterocycloalkyl can be unsubstituted or substituted with one or more substituents which can be the same or different and are independently selected from the group consisting of halogen, alkyl, haloalkyl, —O$R^6$, haloalkoxy, cycloalkyl, heterocycloalkyl, aryl, heteroaryl, —N($R^6$)$_2$, —C(O)$R^6$, —C(O)O$R^6$, —OC(O)$R^6$, —C(O)N($R^6$)$_2$, —N($R^6$)C(O)$R^6$, —N($R^6$)C(O)O$R^6$, —N($R^6$)C(O)N($R^6$)$_2$, —NO$_2$, —CN, —S(O$_2$)$R^6$, and —S(O$_2$)N($R^6$)$_2$; or $R^1$ and $R^2$, taken together with the carbon to which they are shown to be attached in Formula 1, form a carbonyl group with the proviso that G is selected from the group consisting of —O—, —S—, and —N($R^6$)—; or $R^1$ and $R^2$, taken together with the carbon to which they are shown to be attached in Formula 1, form a cycloalkylene ring, wherein said cycloalkylene ring can be unsubstituted or substituted with one or more substituents which can be the same or different and are independently selected from the group consisting of halogen, alkyl, haloalkyl, —O$R^6$, haloalkoxy, cycloalkyl, heterocycloalkyl, aryl, heteroaryl, —N($R^6$)$_2$, —C(O)$R^6$, —C(O)O$R^6$, —OC(O)$R^6$, —C(O)N($R^6$)$_2$, —N($R^6$)C(O)$R^6$, —N($R^6$)C(O)O$R^6$, —N($R^6$)C(O)N($R^6$)$_2$, —NO$_2$, —CN, —S(O$_2$)$R^6$, and —S(O$_2$)N($R^6$)$_2$;

$R^3$ and $R^4$ are independently selected from the group consisting of H, alkyl, cycloalkyl, heterocycloalkyl, aryl, and heteroaryl, wherein each of said alkyl, cycloalkyl, heterocycloalkyl, aryl, or heteroaryl can be unsubstituted or substituted with one or more substituents which can be the same or different and are independently selected from the group consisting of halogen, alkyl, haloalkyl, —O$R^6$, haloalkoxy, cycloalkyl, heterocycloalkyl, aryl, heteroaryl, —N($R^6$)$_2$, —C(O)$R^6$, —C(O)O$R^6$, —OC(O)$R^6$, —C(O)N($R^6$)$_2$, —N($R^6$)C(O)$R^6$, —N($R^6$)C(O)O$R^6$, —N($R^6$)C(O)N($R^6$)$_2$, —NO$_2$, —CN, —S(O$_2$)$R^6$, and —S(O$_2$)N($R^6$)$_2$;

$R^5$ is selected from the group consisting of H, alkyl, cycloalkyl, heterocycloalkyl, aryl, heteroaryl, and —P(O)(OH)$_2$, wherein each of said alkyl, cycloalkyl, heterocycloalkyl, aryl, or heteroaryl can be unsubstituted or substituted with one or more substituents which can be the same or different and are independently selected from the group consisting of halogen, alkyl, haloalkyl, —OR⁶, haloalkoxy, cycloalkyl, heterocycloalkyl, aryl, heteroaryl, —N(R⁶)₂, —C(O)R⁶, —C(O)OR⁶, —OC(O)R⁶, —C(O)N(R⁶)₂, —N(R⁶)C(O)R⁶, —N(R⁶)C(O)OR⁶, —N(R⁶)C(O)N(R⁶)₂, —NO₂, —CN, —S(O₂)R⁶, and —S(O₂)N(R⁶)₂;

R⁶ is selected from the group consisting of H, —CN, alkyl, cycloalkyl, heterocycloalkyl, aryl and heteroaryl, wherein each of said alkyl, cycloalkyl, heterocycloalkyl, aryl and heteroaryl can be unsubstituted or independently substituted with one or more substituents which can be the same or different, and the substituents are independently selected from the group consisting of halogen, —OH, alkyl, haloalkyl, alkoxy, haloalkoxy, cycloalkyl, cycloalkyloxy, heterocycloalkyl, heterocycloalkyloxy, aryl, aryloxy, heteroaryl, and heteroaryloxy;

each R⁷ is independently selected from the group consisting of H, alkyl, cycloalkyl, —OH, alkoxy, cycloalkoxy, halogen, —CN, —NO₂, —CF₃, —CHF₂, —CH₂F, —OCF₃, —OCHF₂, —OCH₂F, —C(O)OR¹¹, —C(O)NR⁹R¹⁰, —N(R⁹)C(O)R¹¹, —N(R⁹)C(O)OR¹², —N(R⁹)C(O)NR⁹R¹⁰, —N(R⁹)S(O₂)R¹², —NR⁹R¹⁰, —S(O₂)NR⁹R¹⁰, —S(O)R¹², —S(O₂)R¹², and (R¹⁵)$_{n8}$-heteroaryl-;

each R⁸ is independently selected from the group consisting of H, alkyl, cycloalkyl, —OH, halogen, —CN, —NO₂, —C(O)CF₃, —CF₃, —CHF₂, —CH₂F, —OCF₃, —OCHF₂, —OCH₂F, alkoxy, cycloalkoxy, —C(O)OR¹¹, —CONR⁹R¹⁰, —NR⁹R¹⁰, —NR⁹COR¹², —NR⁹CO₂R¹¹, —NR⁹CONR⁹R¹⁰, —NR⁹SO₂R¹², —S(O)R¹², and —S(O₂)R¹²;

R⁹ and R¹⁰ are each independently selected from the group consisting of H, alkyl, cycloalkyl, and benzyl; or R⁹ and R¹⁰, taken together with the nitrogen to which they are attached, form a 4-7 membered heteroaryl ring containing from 0-3 additional heteroatoms selected from the group consisting of —O—, —S— and —N(R¹¹)—;

R¹¹ is selected from the group consisting of H, alkyl, and cycloalkyl;

R¹² is selected from the group consisting of alkyl, cycloalkyl, and —CF₃;

each R¹³ is independently selected from the group consisting of —(C(R¹⁷)₂)$_{n7}$-D, wherein D is H, —CF₃, —CHF₂, —CH₂F, —CN, —OH, —O-alkyl, —OCH₂F, —OCHF₂, —OCF₃, —OCH₂CF₃, —O-cycloalkyl, —O-alkyl-cycloalkyl, —NR¹⁸R¹⁹, —SO₂NR¹⁸R¹⁹, —NR¹¹SO₂R¹⁸, —NR¹¹C(O)R¹⁹, —NR¹¹C(O)OR¹⁸, —NR¹¹C(O)NR¹⁸R¹⁹), —C(O)NR¹⁸R¹⁹, —C(O)OR¹⁸, -cycloalkyl, (R⁷)$_{n7}$- aryl-, (R⁸)$_{n8}$-heteroaryl-, —OC(O)R¹⁹, —OC(O)NR¹⁸R¹⁹, —C(=NOR¹⁹)(R¹⁸), —C(O)R¹⁸, —C(OR¹¹)(R¹⁸)(R¹⁹), heterocycloalkenyl optionally substituted by 1 to 4 substituents independently selected from the group consisting of R²¹ and R²²,

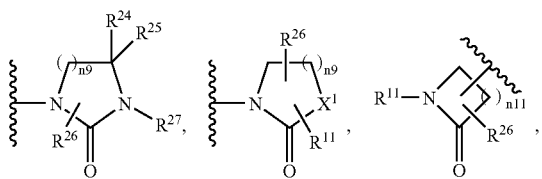

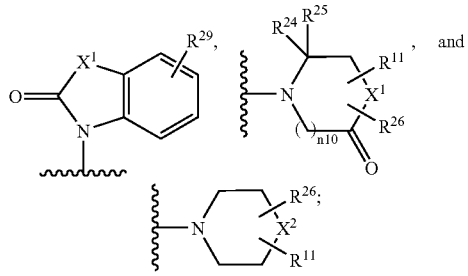

R¹⁴ is H, alkyl, haloalkyl, aryl, heteroaryl, hydroxyalkyl, cycloalkyl, heterocycloalkyl, —S(O)R⁶, —S(O₂)R⁶, —C(O)OR⁶, —C(O)R⁶, and —C(O)N(R⁶)₂;

R¹⁵ is H, alkyl, cycloalkyl, alkoxy, —OH, —CN, —NO₂, —CF₃, —CHF₂, —CH₂F, —OCF₃, —OCHF₂, —OCH₂F, cycloalkoxy, —C(O)OR¹¹, —C(O)NR⁹R¹⁰, —N(R⁹)C(O)R¹¹, —N(R⁹)C(O)OR¹², —N(R⁹)C(O)NR⁹R¹⁰, —N(R⁹)S(O₂)R¹², —NR⁹R¹⁰, —S(O₂)NR⁹R¹⁰, —S(O)R¹², —S(O₂)R¹²;

each R¹⁷ is independently H or alkyl;

R¹⁸ and R¹⁹ are each independently selected from the group consisting of H, alkyl, cycloalkyl, cycloalkylalkyl, —CH₂CF₃, aryl and heteroaryl; or R¹⁸ and R¹⁹, together with the nitrogen atom to which they are both attached, form a 4- to 7-membered saturated or unsaturated ring that is optionally substituted with —OR¹¹, where one of the carbon atoms in the ring is optionally replaced by a heteroatom selected from the group consisting of —O—, —S— and —NR²⁰—;

R²⁰ is H, alkyl, cycloalkyl, cycloalkylalkyl or hydroxyalkyl;

R²¹ and R²², together with the carbon atom to which they are both attached, form —C(O)—, —C(S)—, a cyclopropyl ring or —C(NR²³)—;

R²³ is H, alkyl, cycloalkyl, cycloalkylalkyl, —NO₂, —CN or OR¹¹;

R²⁴ and R²⁵ are each independently selected from the group consisting of H and alkyl; or R²⁴ and R²⁵, together with the carbon atom to which they are both attached, form a —C(O)— or cyclopropyl group;

R²⁶ is H, —OH or alkyl;

R²⁷ is H, alkyl, cycloalkyl, cycloalkylalkyl, —P(O)(OH)₂, allyl, hydroxyalkyl, alkoxyalkyl, —SO₂R²⁸ or —(CH₂)₂—N(R¹¹)—SO₂—R²⁸;

R²⁸ is alkyl, cycloalkyl, —CF₃ or —CH₂CF₃;

R²⁹ is 1 to 3 substituents independently selected from the group consisting of H, alkyl, —OH, alkoxy and halogen;

X¹ is —NR²⁷—, —O—, —S—, —S(O)—, —S(O₂)—, —CH₂—, —CF₂— or —CR¹¹F—; and

X² is —NR²⁰—, —N(C(O)NR¹⁸R¹⁹)—, —N(C(O)OR¹⁸)—, —N(S(O₂)R²⁸)—, —N(C(O)R¹¹)—, —N(S(O₂)NHR¹⁸)—, —O—, —S—, —S(O)—, —S(O₂)—, —CH₂—, —CF₂— or —CR¹¹F—.

In another embodiment of the compounds of Formula 1,

R¹ and R² are independently selected from the group consisting of H, (C₁-C₆)alkyl, hydroxy(C₁-C₃)alkyl, (C₃-C₈)cycloalkyl, —CH₂F, —CHF₂, and —CF₃; or R¹ and R², taken together with the carbon to which they are shown to be attached in Formula 1, form a carbonyl group; or $R^1$ and $R^2$, taken together with the carbon to which they are shown to be attached in Formula 1, form a $(C_3-C_6)$cycloalkylene ring;

$R^3$ and $R^4$ are H;

$R^5$ is selected from the group consisting of H, $(C_1-C_6)$alkyl, hydroxy$(C_1-C_3)$alkyl, $(C_3-C_8)$cycloalkyl, —$CH_2F$, —$CHF_2$, and —$CF_3$;

G is —O— or —$N(R^{14})$—;

$R^{14}$ is H, $(C_1-C_6)$alkyl, hydroxy$(C_1-C_3)$alkyl, $(C_3-C_8)$cycloalkyl, —$CH_2F$, —$CHF_2$, —$CF_3$;

$Ar^1$ is monosubstituted phenyl; and $Ar^2$ is disubstituted phenyl.

In another embodiment of the compounds of Formula 1, $Ar^1$ is a monosubstituted phenyl.

In another embodiment of the compounds of Formula 1, $Ar^1$ is phenyl;

In another embodiment of the compounds of Formula 1, $Ar^2$ is a disubstituted phenyl.

In another embodiment of the compounds of Formula 1, $Ar^2$ is a 3,5-disubstituted phenyl.

In another embodiment of the compounds of Formula 1, $Ar^2$ is 3,5-bis(trifluoromethyl)phenyl.

In another embodiment of the compounds of Formula 1, $Ar^1$ is phenyl and $Ar^2$ is 3,5-bis(trifluoromethyl)phenyl.

In another embodiment of the compounds of Formula 1, G is —O—.

In another embodiment of the compounds of Formula 1, $R^1$ and $R^2$ are each independently H or $C_1-C_6$ alkyl.

In another embodiment of the compounds of Formula 1, $R^1$ is —$CH_3$; and $R^2$ is —H.

In another embodiment of the compounds of Formula 1, at least one of $R^3$ and $R^4$ is H.

In another embodiment of the compounds of Formula 1, both $R^3$ and $R^4$ are H.

In another embodiment of the compounds of Formula 1, $R^5$ is H.

In another embodiment of the compounds of Formula 1, n1 is 1 or 2.

In another embodiment of the compounds of Formula 1, n2 is 0 or 1.

In another embodiment of the compounds of Formula 1, n1 and n2 are both 1.

In another embodiment of the compounds of Formula 1, n1 is 1 and n2 is 0.

In another embodiment of the compounds of Formula 1, n1 is 2 and n2 is 0.

In another embodiment of the compounds of Formula 1, X is selected from the group consisting of —$N(R^6)$— and —O—.

In another embodiment of the compounds of Formula 1, X is —$N(R^6)$—.

In another embodiment of the compounds of Formula 1, X is —O—.

In another embodiment of the compounds of Formula 1, Y is selected from the group consisting of —$N(R^6)$—, —O—, —$CH_2$—, —$(CH_2)_2O$—, —$O(CH_2)_2$—, —$(CH_2)_2$—, —$CH_2N(R^6)$—, and —$N(R^6)CH_2$—.

In another embodiment of the compounds of Formula 1, Y is —$N(R^6)$—.

In another embodiment of the compounds of Formula 1, Y is —O—.

In another embodiment of the compounds of Formula 1, Y is —$CH_2$—.

In another embodiment of the compounds of Formula 1, Y is —$(CH_2)_2O$—.

In another embodiment of the compounds of Formula 1, Y is —$O(CH_2)_2$—.

In another embodiment of the compounds of Formula 1, Y is —$(CH_2)_2$—.

In another embodiment of the compounds of Formula 1, Y is —$CH_2N(R^6)$—.

In another embodiment of the compounds of Formula 1, Y is —$N(R^6)CH_2$—.

In another embodiment of the compounds of Formula 1, Z is —C(O)—.

In another embodiment of the compounds of Formula 1, $R^{13}$ is H.

In yet another embodiment, the compounds of Formula 1 can be represented by Formula 2:

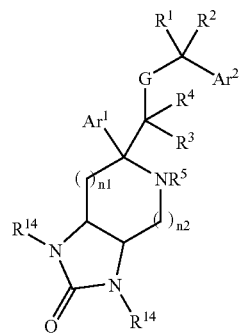

Formula 2 or a pharmaceutically acceptable salt and/or solvate thereof.

In yet another embodiment, the compounds of Formula 1 can be represented by Formula 3:

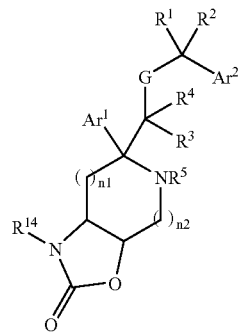

Formula 3 or a pharmaceutically acceptable salt and/or solvate thereof.

In yet another embodiment, the compounds of Formula 1 can be represented by Formula 4:

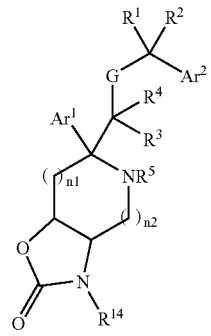

Formula 4 or a pharmaceutically acceptable salt, or solvate thereof.

In yet another embodiment, the compounds of Formula 1 can be represented by Formula 5:

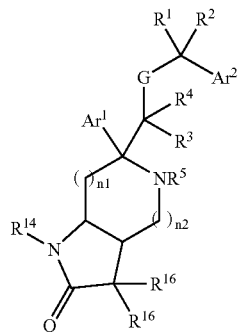

Formula 5 where $R^{16}$ is H, F, alkyl, or each $R^{16}$ together with the ring carbon atom to which they are shown attached in Formula 5 defines a cycloalkyl ring.

In yet another embodiment, the compounds of Formula 1 can be represented by Formula 6:

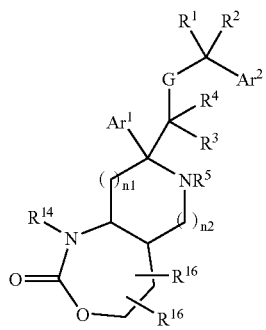

Formula 6 where $R^{16}$ is H, F, alkyl, or each $R^{16}$ together with the ring carbon atom or atoms to which they are shown attached in Formula 6 defines a cycloalkyl ring.

In yet another embodiment, the compounds of Formula 1 can be represented by Formula 7:

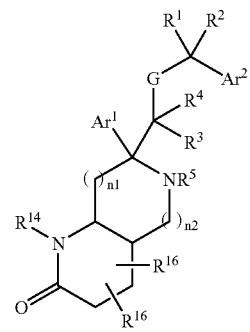

Formula 7 where $R^{16}$ is H, F, alkyl, or each $R^{16}$ together with the ring carbon atom or atoms to which they are shown attached in Formula 7 defines a cycloalkyl ring.

In yet another embodiment, the compounds of Formula 1 can be represented by Formula 8:

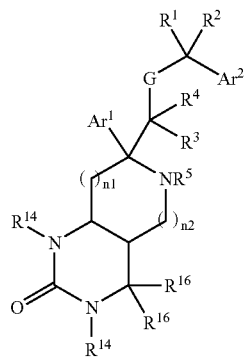

Formula 8 where $R^{16}$ is H, F, alkyl, or each $R^{16}$ together with the ring carbon atom to which they are shown attached in Formula 8 defines a cycloalkyl ring.

In still another embodiment, the compounds of Formula 1 can be represented by Formula 9:

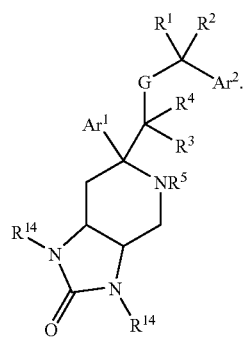

Formula 9

In still another embodiment, the compounds of Formula 1 can be represented by Formula 10:

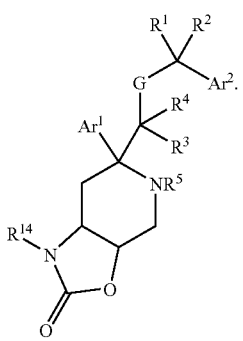

Formula 10

In still another embodiment, the compounds of Formula 1 can be represented by Formula 11:

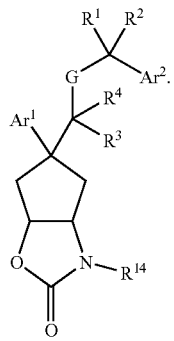

Formula 11

In still another embodiment, the compounds of Formula 1 can be represented by Formula 12:

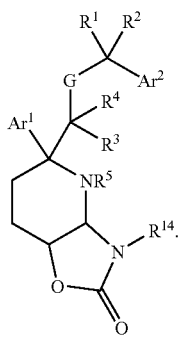

Formula 12

In still another embodiment, the compounds of Formula 1 can be represented by Formula 13:

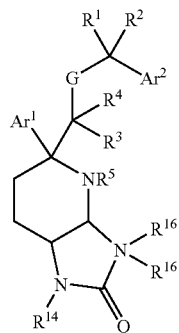

Formula 13 where $R^{16}$ is H, F, alkyl, or each $R^{16}$ together with the ring carbon atom to which they are shown attached in Formula 13 defines a cycloalkyl ring.

In still another embodiment, the compounds of Formula 1 can be represented by Formula 14:

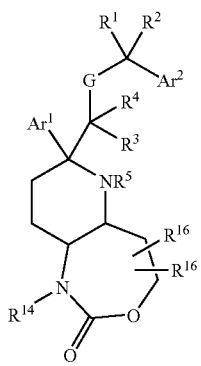

Formula 14 where $R^{16}$ is H, F, alkyl, or each $R^{16}$ together with the ring carbon atom or atoms to which they are shown attached in Formula 14 defines a cycloalkyl ring.

In still another embodiment, the compounds of Formula 1 can be represented by Formula 15:

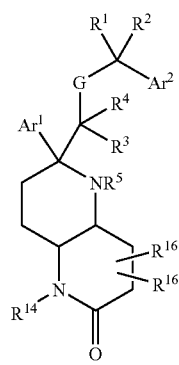

Formula 15 where $R^{16}$ is H, F, alkyl, or each $R^{16}$ together with the ring carbon atom or atoms to which they are shown attached in Formula 15 defines a cycloalkyl ring.

In still another embodiment, the compounds of Formula 1 can be represented by Formula 16:

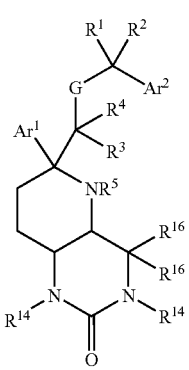

Formula 16 where $R^{16}$ is H, F, alkyl, or each $R^{16}$ together with the ring carbon atom to which they are shown attached in Formula 16 defines a cycloalkyl ring.
In still another embodiment, the compounds of Formula 1 can be represented by Formula 17:
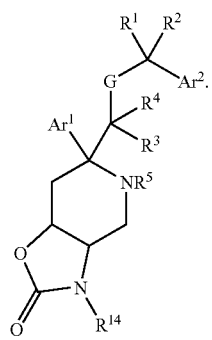
Formula 17
In still yet another embodiment, a compound of Formula 1 is selected from the compounds of the formulae:
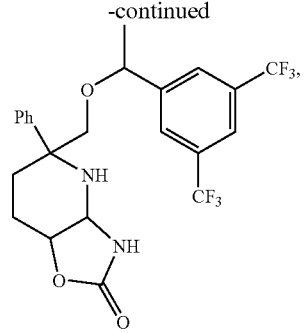
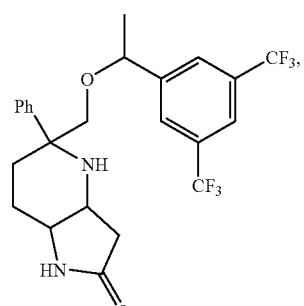
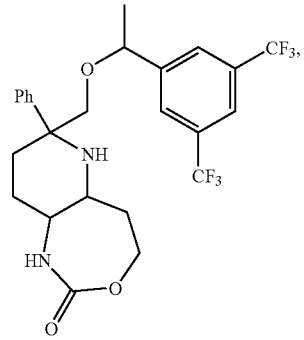
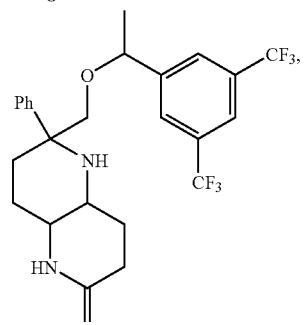
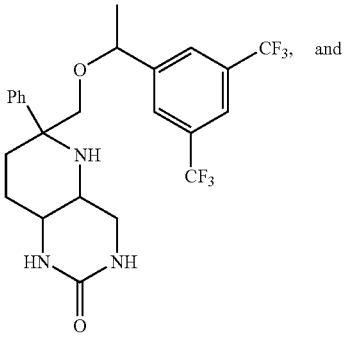
and -continued

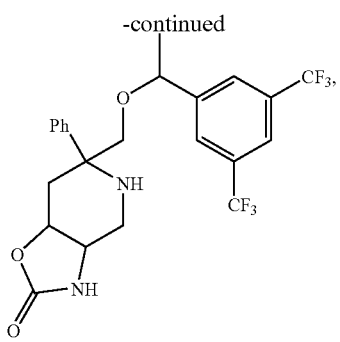

or a pharmaceutically acceptable salt and/or solvate thereof.

In still yet another embodiment, the compound of Formula 1 is a compound of the formula:

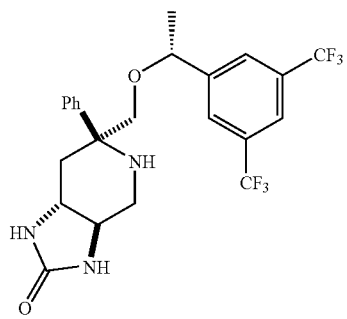

or a pharmaceutically acceptable salt and/or solvate thereof.

In still yet another embodiment, the compound of Formula 1 is a compound of the formula:

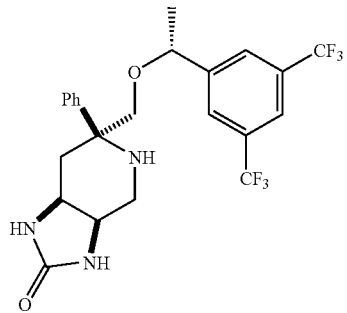

or a pharmaceutically acceptable salt and/or solvate thereof.

In still yet another embodiment, the compound of Formula 1 is a compound of the formula:

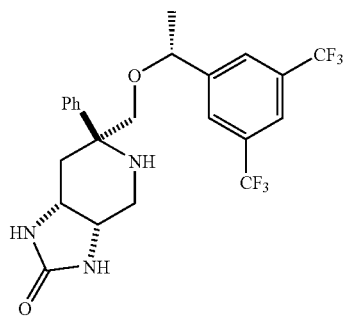

or a pharmaceutically acceptable salt and/or solvate thereof.

In still yet another embodiment, the compound of Formula 1 is a compound of the formula:

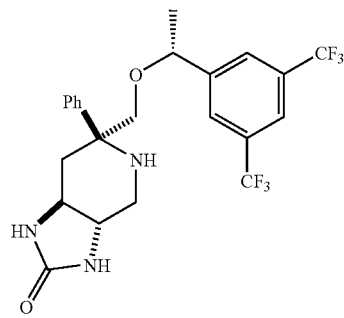

or a pharmaceutically acceptable salt and/or solvate thereof.

In still yet another embodiment, the compound of Formula 1 is a compound of the formula:

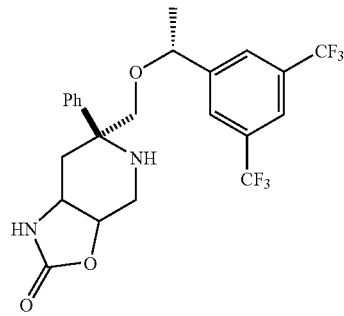

or a pharmaceutically acceptable salt, or solvate thereof.

In still yet another embodiment, the compound of Formula 1 is a compound of the formula:

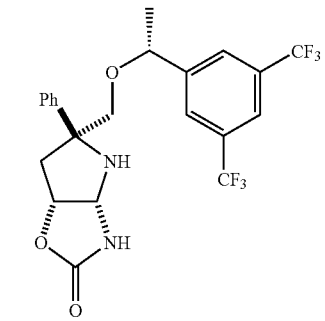

or a pharmaceutically acceptable salt and/or solvate thereof.

In still yet another embodiment, the compound of Formula 1 is a compound of the formula:

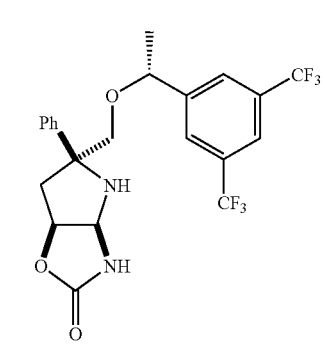

or a pharmaceutically acceptable salt and/or solvate thereof.

In still yet another embodiment, the compound of Formula 1 is a compound of the formula:

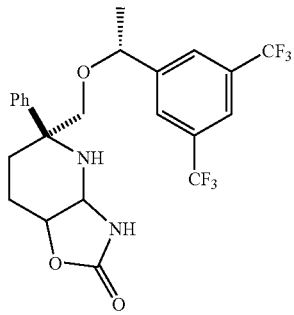

or a pharmaceutically acceptable salt and/or solvate thereof.

In still yet another embodiment, the compound of Formula 1 is a compound of the formula:

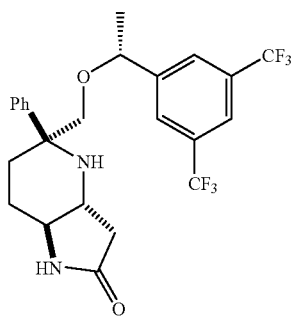

or a pharmaceutically acceptable salt and/or solvate thereof.

In still yet another embodiment, the compound of Formula 1 is a compound of the formula:

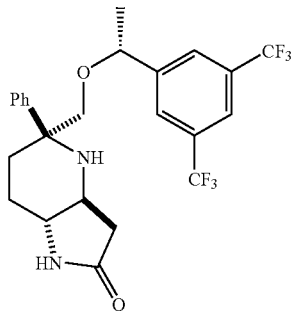

or a pharmaceutically acceptable salt and/or solvate thereof.

In still yet another embodiment, the compound of Formula 1 is a compound of the formula:

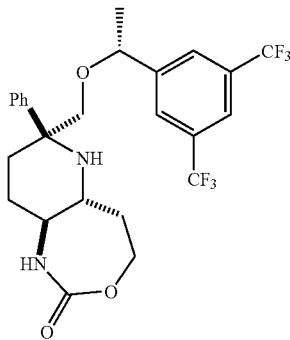

or a pharmaceutically acceptable salt and/or solvate thereof.

In still yet another embodiment, the compound of Formula 1 is a compound of the formula:

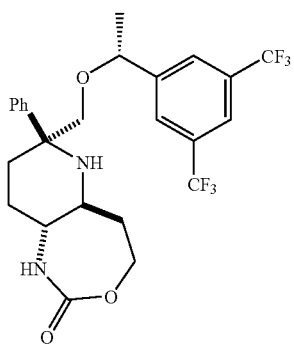

or a pharmaceutically acceptable salt and/or solvate thereof.

In still yet another embodiment, the compound of Formula 1 is a compound of the formula:

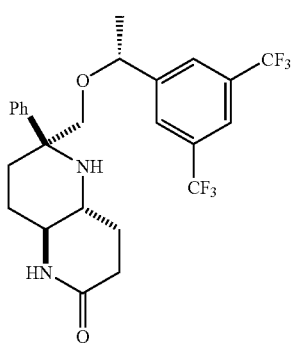

or a pharmaceutically acceptable salt and/or solvate thereof.

In still yet another embodiment, the compound of Formula 1 is a compound of the formula:

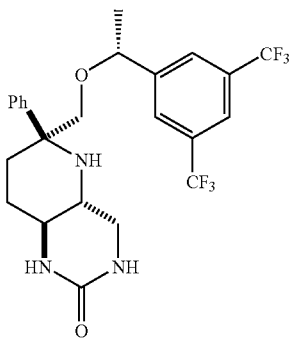

or a pharmaceutically acceptable salt and/or solvate thereof.

In still yet another embodiment, the compound of Formula 1 is a compound of the formula:

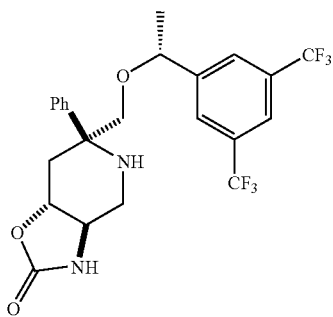

or a pharmaceutically acceptable salt and/or solvate thereof.

In still yet another embodiment, the compound of Formula 1 is a compound of the formula:

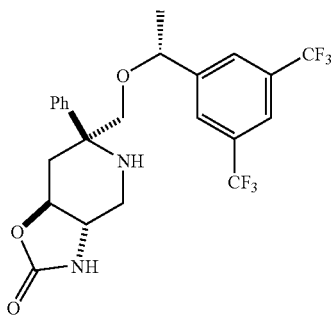

or a pharmaceutically acceptable salt and/or solvate thereof.

In an additional embodiment, the present invention is directed to a pharmaceutical composition comprising an effective amount of at least one compound of Formula 1, or a pharmaceutically acceptable salt and/or solvate thereof, and at least one pharmaceutically acceptable carrier.

In an additional embodiment, this invention is directed to a kit comprising two or more containers in a single package, wherein each container in the package comprises a pharmaceutical composition. At least one container of the package comprises an effective amount of the compound of Formula I, or a pharmaceutically acceptable salt and/or solvate thereof in a pharmaceutically acceptable carrier, and at least one other container of the package comprises another therapeutic agent in a pharmaceutically acceptable carrier. The pharmaceutical compositions of the kit may be used in combination.

In an additional embodiment, the present invention is directed to a method for affecting an $NK_1$ receptor in a patient comprising administering to the patient an effective amount of at least one compound of Formula 1 or a pharmaceutically acceptable salt and/or solvate thereof.

In an additional embodiment, the present invention is directed to a method for treating an $NK_1$ receptor mediated condition or disease (i.e., a disease associated with an $NK_1$ receptor, or a disease involving an $NK_1$ receptor in part of the disease process) in a patient in need of such treatment comprising administering to the patient an effective amount of at least one compound of Formula 1 or a pharmaceutically acceptable salt and/or solvate thereof.

In still an additional embodiment, the present invention is directed to a method of treating a disease (or disorder or condition) in a patient in need of such treatment, wherein the disease is selected from the group consisting of: (1) respiratory diseases (e.g., chronic lung disease, bronchitis, pneumonia, asthma, allergy, cough and bronchospasm), (2) inflammatory diseases (e.g., arthritis and psoriasis), (3) skin disorders (e.g., atopic dermatitis and contact dermatitis), (4) ophthalmological disorders (e.g., retinitis, ocular hypertension and cataracts), (5) central nervous system conditions, such as depressions (e.g., neurotic depression), anxieties (e.g., general anxiety, social anxiety and panic anxiety disorders), phobias (e.g., social phobia), and bipolar disorder, (6) addictions (e.g., alcohol dependence and psychoactive substance abuse), (7) epilepsy, (8) nociception, (9) psychosis, (10) schizophrenia, (11) Alzheimer's disease, (12) AIDS related dementia, (13) Towne's disease, (14) stress related disorders (e.g., post traumatic stress disorder), (15) obsessive/compulsive disorders, (16) eating disorders (e.g., bulimia, anorexia nervosa and binge eating), (17) sleep disorders, (18) mania, (19) premenstrual syndrome, (20) gastrointestinal disorders (e.g., irritable bowel syndrome, Crohn's disease, colitis, and emesis), (21) atherosclerosis, (22) fibrosing disorders (e.g., pulmonary fibrosis), (23) obesity, (24) Type II diabetes, (25) pain related disorders (e.g., headaches, such as migraines, neuropathic pain, post-operative pain, and chronic pain syndromes), (26) bladder and genitourinary disorders (e.g., interstitial cystitis and urinary incontinence), (27) emesis (e.g., chemotherapy-induced (e.g., induced by cisplatin, doxorubicin, and taxane), radiation-induced, motion sickness, ethanol-induced, and post operative nausea and vomiting), and (28) nausea, comprising administering to the patient an effective amount of at least one (e.g., one) compound of Formula 1 or a pharmaceutically acceptable salt and/or solvate thereof.

In still an additional embodiment, the present invention is directed to a method of treating a disease (or disorder or condition) in a patient in need of such treatment, wherein the disease is selected from the group consisting of: respiratory diseases (e.g., cough), depression, anxiety, phobia, bipolar disorder, alcohol dependence, psychoactive substance abuse, nociception, psychosis, schizophrenia, stress related disorders, obsessive/compulsive disorder, bulimia, anorexia nervosa, binge eating, sleep disorders, mania, premenstrual syndrome, gastrointestinal disorders, obesity, pain related disorders (e.g., headaches, such as migraines, neuropathic pain, post-operative pain, and chronic pain syndromes), bladder disorders, genitourinary disorders, emesis and nausea, comprising administering to the patient an effective amount of at least one compound of Formula 1 or a pharmaceutically acceptable salt and/or solvate thereof.

In still an additional embodiment, the present invention also is directed to a method of treating a disease (or disorder or condition) wherein there is microvascular leakage and mucus secretion in a patient in need of such treatment, comprising administering to the patient an effective amount of at least one compound of Formula 1 or a pharmaceutically acceptable salt and/or solvate thereof.

In still an additional embodiment, the present invention also is directed to a method of treating asthma, emesis, nausea, depressions, anxieties, cough and pain related disorders in a patient in need of such treatment comprising administering to the patient an effective amount of at least one compound of Formula 1 or a pharmaceutically acceptable salt and/or solvate thereof.

In still an additional embodiment, the present invention also is directed to a method of treating emesis, depression, anxiety and cough in a patient in need of such treatment comprising administering to the patient an effective amount of at least one compound of Formula 1 or a pharmaceutically acceptable salt and/or solvate thereof.

In still an additional embodiment, the present invention also is directed to a method for antagonizing an effect of a Substance P at a neurokinin-1 receptor site in a patient in need of such treatment, comprising administering to the patient at least one compound of Formula 1 or a pharmaceutically acceptable salt and/or solvate thereof.

In still an additional embodiment, the present invention also is directed to a method for the blockade of $NK_1$ receptors in a patient in need of such treatment, comprising administering to the patient at least one compound of Formula 1 or a pharmaceutically acceptable salt and/or solvate thereof.

In still an additional embodiment, the present invention also is directed to a method for treating depression and/or anxiety in a patient in need of such treatment comprising administering to the patient an effective amount of one or more compounds of Formula 1 or a pharmaceutically acceptable salt and/or solvate thereof, in combination with an effective amount of one or more anti-depressant agents and/or one or more anti-anxiety agents.

In still an additional embodiment, the present invention also is directed to a method of treating an $NK_1$ receptor mediated disease (or disorder or condition) in a patient in need of such treatment comprising administering to the patient an effective amount of one or more compounds of Formula 1 or a pharmaceutically acceptable salt and/or solvate thereof, in combination with an effective amount of one or more selective serotonin reuptake inhibitors ("SSRIs").

In still an additional embodiment, the present invention also is directed to a method of treating depression and/or anxiety in a patient in need of such treatment comprising administering to the patient an effective amount of one or more compounds of Formula 1 or a pharmaceutically acceptable salt and/or solvate thereof, in combination with an effective amount of one or more selective serotonin reuptake inhibitors.

In yet an additional embodiment, the present invention also is directed to a method of treating an $NK_1$ receptor mediated disease (or disorder or condition) in a patient in need of such treatment comprising administering to the patient an effective amount of at least one compound of Formula 1 or a pharmaceutically acceptable salt and/or solvate thereof, in combination with at least one therapeutic agent selected from the group consisting of: other types of $NK_1$ receptor antagonists (e.g., $NK_1$ receptor antagonists other than those according to Formula 1 of the present invention), prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists (e.g., ondansetron), serotonin 5-$HT_{2c}$ receptor agonists, nociceptin receptor agonists, glucocorticoids (e.g., dexamethasone), rho kinase inhibitors, potassium channel modulators and inhibitors of multi-drug resistance protein 5.

In yet an additional embodiment, the invention also is directed to a method for treating an $NK_1$ mediated disease (or disorder or condition) in a patient in need of such treatment comprising administering to the patient an effective amount of a compound of Formula 1 or a pharmaceutically acceptable salt and/or solvate thereof, in combination at least one therapeutic agent selected from the group consisting of: prostanoids, such as prostaglandin E1; α-adrenergic agonists, such as phentolamine mesylate; dopamine receptor agonists, such as apomorphine; angiotensin II antagonists, such as losartan, irbesartan, valsartan and candesartan; $ET_A$ antagonists, such as bosentan and ABT-627; serotonin 5-$HT_3$ receptor antagonists, such as ondansetron; and glucocorticoids, such as dexamethasone.

In yet an additional embodiment, the invention also is directed to a method for treating an $NK_1$ mediated disease (or disorder or condition) in a patient in need of such treatment comprising administering to the patient an effective amount of at least one compound of Formula 1 or a pharmaceutically acceptable salt and/or solvate thereof, in combination with an effective amount of at least one therapeutic agent selected from the group consisting of: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and inhibitors of multi-drug resistance protein 5.

In yet an additional embodiment, the invention also is directed to a method for treating emesis, nausea and/or vomiting in a patient in need of such treatment comprising administering to the patient an effective amount of at least one compound of Formula 1 or a pharmaceutically acceptable salt and/or solvate thereof, in combination with and effective amount of at least one serotonin 5-$HT_3$ receptor antagonist (e.g., ondansetron) and/or at least one glucocorticoid (e.g., dexamethasone).

In still yet an additional embodiment, the present invention also is directed to a kit comprising, in separate containers in a single package, pharmaceutical compositions for use in combination to treat an $NK_1$ receptor mediated disease (or disorder or condition), wherein one container comprises a pharmaceutical composition comprising an effective amount of a compound of Formula 1 or a pharmaceutically acceptable salt and/or solvate thereof, in a pharmaceutically acceptable carrier, and wherein, a separate container comprises a pharmaceutical composition comprising another therapeutic agent in a pharmaceutically acceptable carrier, the therapeutic agent being selected from the group consisting of: SSRIs, other types of $NK_1$ receptor antagonists, prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, ETA antagonists, renin inhibitors, serotonin 5-$HT_3$ receptor antagonists, serotonin 5-$HT_{2c}$ receptor agonists, nociceptin receptor agonists, glucocorticoids, rho kinase inhibitors, potassium channel modulators and inhibitors of multi-drug resistance protein 5.

In still yet an additional embodiment, the present invention also is directed to a kit comprising, in separate containers in a single package, pharmaceutical compositions for use in combination to treat depression and/or anxiety, wherein one container comprises a pharmaceutical composition comprising an effective amount of a compound of Formula 1 or a pharmaceutically acceptable salt and/or solvate thereof, in a pharmaceutically acceptable carrier, and wherein, a separate container comprises a pharmaceutical composition comprising an antidepressant agent in a pharmaceutically acceptable carrier, and/or wherein a separate container comprises a pharmaceutical composition comprising an antianxiety agent in a pharmaceutically acceptable carrier.

In still yet an additional embodiment, the present invention also is directed to a kit comprising, in separate containers in a single package, pharmaceutical compositions for use in combination to treat an $NK_1$ receptor mediated disease, wherein one container comprises a pharmaceutical composition comprising an effective amount of a compound of Formula 1 or a pharmaceutically acceptable salt and/or solvate thereof, in a pharmaceutically acceptable carrier, and wherein, a separate container comprises a pharmaceutical composition comprising an SSRI in a pharmaceutically acceptable carrier.

In still yet an additional embodiment, the present invention also is directed to a kit comprising, in separate containers in a single package, pharmaceutical compositions for use in combination to treat depression and/or anxiety, wherein one container comprises a pharmaceutical composition comprising an effective amount of a compound of Formula 1 or a pharmaceutically acceptable salt and/or solvate thereof, in a pharmaceutically acceptable carrier, and wherein, a separate container comprises a pharmaceutical composition comprising an SSRI in a pharmaceutically acceptable carrier.

In still yet an additional embodiment, the present invention also is directed to a kit comprising, in separate containers in a single package, pharmaceutical compositions for use in combination to treat emesis and/or nausea, wherein one container comprises a pharmaceutical composition comprising an effective amount of a compound of Formula 1 or a pharmaceutically acceptable salt and/or solvate thereof, in a pharmaceutically acceptable carrier, and wherein, a separate container comprises a pharmaceutical composition comprising a serotonin 5-$HT_3$ receptor antagonist in a pharmaceutically acceptable carrier, and/or wherein a separate container comprises a pharmaceutical composition comprising a glucocorticoid in a pharmaceutically acceptable carrier.

In still yet an additional embodiment, the present invention also is directed to a kit comprising, in separate containers in a single package, pharmaceutical compositions for use in combination to treat emesis and/or nausea, wherein one container comprises a pharmaceutical composition comprising an effective amount of a compound of Formula 1 or a pharmaceutically acceptable salt and/or solvate thereof, in a pharmaceutically acceptable carrier, and wherein, a separate container comprises ondansetron, and/or wherein a separate container comprises dexamethasone.

Other features and advantages of the invention will be apparent from the following detailed description, and from the claims.

DETAILED DESCRIPTION OF THE INVENTION

Except where stated otherwise, the following definitions apply throughout the specification and claims. When any variable occurs more than one time in any moiety, its definition on each occurrence is independent of its definition at every other occurrence. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Ac means acetyl.
Boc means t-butoxycarbonyl.
Bu means butyl.
t-Bu or $Bu^t$ means tertiary-butyl.
Cbz means carbobenzoxy (i.e., Ph-$CH_2$—O—C(O)—).
DIEA means diisopropylethyl amine.
DMPU means N,N H-dimethyl propylene urea.
DPPA means diphenylphosphorazide.
Et means ethyl.
HOTs means p-toluene sulfonic acid.
HPLC means High Performance Liquid Chromatography.
LiHMDS means lithium hexamethyldisilazide.
Me means methyl.
MS means mass spectroscopy.
Ni (Ra) means Raney Ni.
OD means optical density.
Ph means phenyl
i-PA (or IPA or iPA) means isopropyl.
PPTS means pyridinium p-toluenesulfonic acid.
PTSA means p-toluene sulfonic acid.
THF means tetrahydrofuran.
TLC means Thin Layer Chromatography.
"Patient" includes both human and animals.
"Mammal" means humans and other mammalian animals.

Portions of chemical formulae enclosed in parentheses and/or brackets denote pendant groups. For example, —C(O)— refers to a carbonyl group (i.e.,

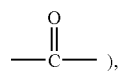

),

—N(alkyl)- refers to a divalent amine group with a pendant alkyl group (i.e.,

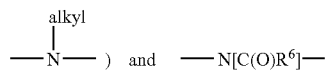

refers to

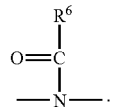

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain that may be straight or branched.

The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain, which may be straight or branched. The term "alkenyl" includes substituted alkenyl which means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl (i.e., vinyl), propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain that may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, tetrazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. A non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred halogens are fluorine, chlorine and bromine. "Halogen" or "halo" substituted groups (e.g., haloalkyl groups) refers to groups substituted with one or more fluorine, chlorine, bromine, and/or iodine atoms.

"Ring system substituent" means a substituent attached to an aromatic or non-aromatic ring system, which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

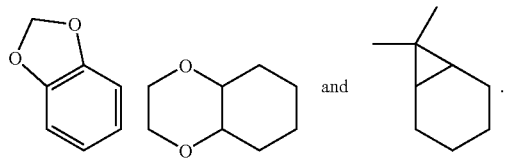

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may be present in protected form such as, for example, an —N(Boc), —N(CBz), —N(Tos) group and the like; such protected functional groups are also considered part of this invention. The heterocycloalkyl can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

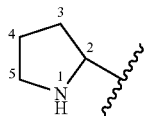

there is no —OH attached directly to carbons marked 2 and 5.

It should also be noted that tautomeric forms such as, for example, the moieties:

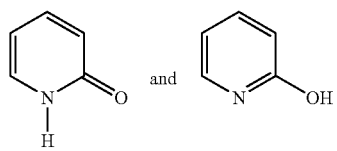

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. The "alkyl" portion of the hydroxyalkyl is preferably a lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a ring system (e.g., cycloalkyl, heterocycloalkyl, aryl, or heteroaryl) is substituted with a number of substituents varying within an expressly defined range, it is understood that the total number of substituents does not exceed the normal available valencies under the existing conditions. Thus, for example, a phenyl ring substituted with "n" substituents (where "n" ranges from 0 to 5) can have 0 to 5 substituents, whereas it is understood that a pyridinyl ring substituted with "n" substituents has a number of substituents ranging from 0 to 4.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York, herein incorporated by reference.

When any variable (e.g., aryl, heterocycloalkyl, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

"Alkylheteroaryl" means an alkyl group attached to a parent moiety via a heteroaryl group.

"Alkylsulfinyl" means an alkyl-S(O)— group. Preferred groups are those in which the alkyl group is lower alkyl. The bond to the parent moiety is through the sulfinyl.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylsulfinyl" means an aryl-S(O)— group. Non-limiting examples of suitable arylsulfinyl groups include phenylsulfinyl and naphthylsulfinyl. The bond to the parent moiety is through the sulfinyl.

A carbamate group means a —O—C(O)—N(alkyl or aryl)- group, and a urea group means a —N(alkyl or aryl)-C(O)—N(alkyl or aryl)- group. Representative carbamate and urea groups may include the following:

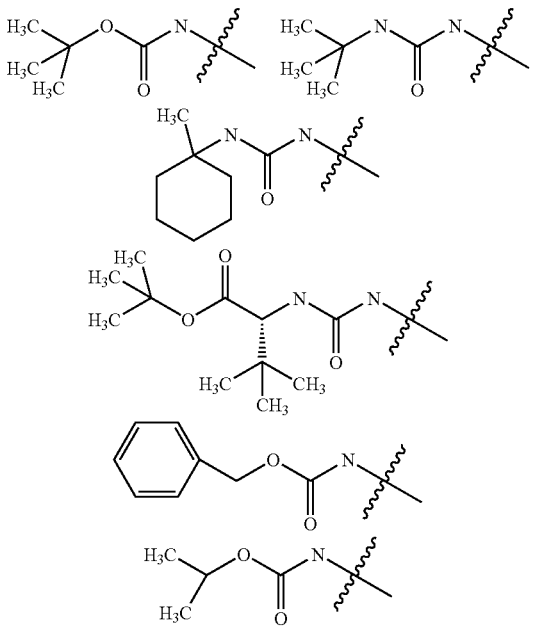

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Cycloalkylamino" means a cycloalkyl group as defined herein attached to the parent moiety through a nitrogen atom.

"Cycloalkylaminocarbonyl" means a cyclic alkyl group attached to a nitrogen atom, which is attached to a carbonyl group; the whole may be referred to as a substituted amide.

"Heteroalkyl" means an alkyl as defined herein, in which one or more of the atoms is an element other than carbon, for example nitrogen, oxygen or sulfur, alone or in combination.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkylthio" means a heteroaryl-alkyl-S group wherein the group is attached to the parent moiety through the sulfur.

"Heteroarylsulfinyl" means a heteroaryl-S(O)— group wherein the heteroaryl is as defined herein and the heteroarylsulfinyl group is attached to the parent moiety through the sulfinyl.

"Heteroarylsulfonyl" means a heteroaryl-S(O$_2$)— group wherein the heteroaryl is as defined herein and the heteroarylsulfonyl group is attached to the parent moiety through the sulfonyl.

"Heteroarylthio" means a heteroaryl-S— group wherein the heteroaryl is as defined herein and the heteroarylsulfinyl group is attached to the parent moiety through the sulfur.

"Heterocycloalkenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocycloalkenyl rings contain about 5 to about 6 ring atoms. The prefix aza, oxa or thia before the heterocycloalkenyl root name means that at least a nitrogen, oxygen or sulfur atom respectively is present as a ring atom. The heterocycloalkenyl can be optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of suitable monocyclic azaheterocycloalkenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocycloalkenyl groups include 3,4-dihydro-2H-pyran, dihydrofuranyl, fluorodihydrofuranyl, and the like. Non-limiting example of a suitable multicyclic oxaheterocycloalkenyl group is 7-oxabicyclo[2.2.1]heptenyl. Non-limiting examples of suitable monocyclic thiaheterocycloalkenyl rings include dihydrothiophenyl, dihydrothiopyranyl, and the like.

"Heterocyclic" means, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl.

"Sulfonamide" means a sulfonyl group attached to a parent moiety through an amide.

As is well known in the art, a bond drawn from a particular atom wherein no moiety is depicted at the terminal end of the bond indicates a methyl group bound through that bond to the atom. For example:

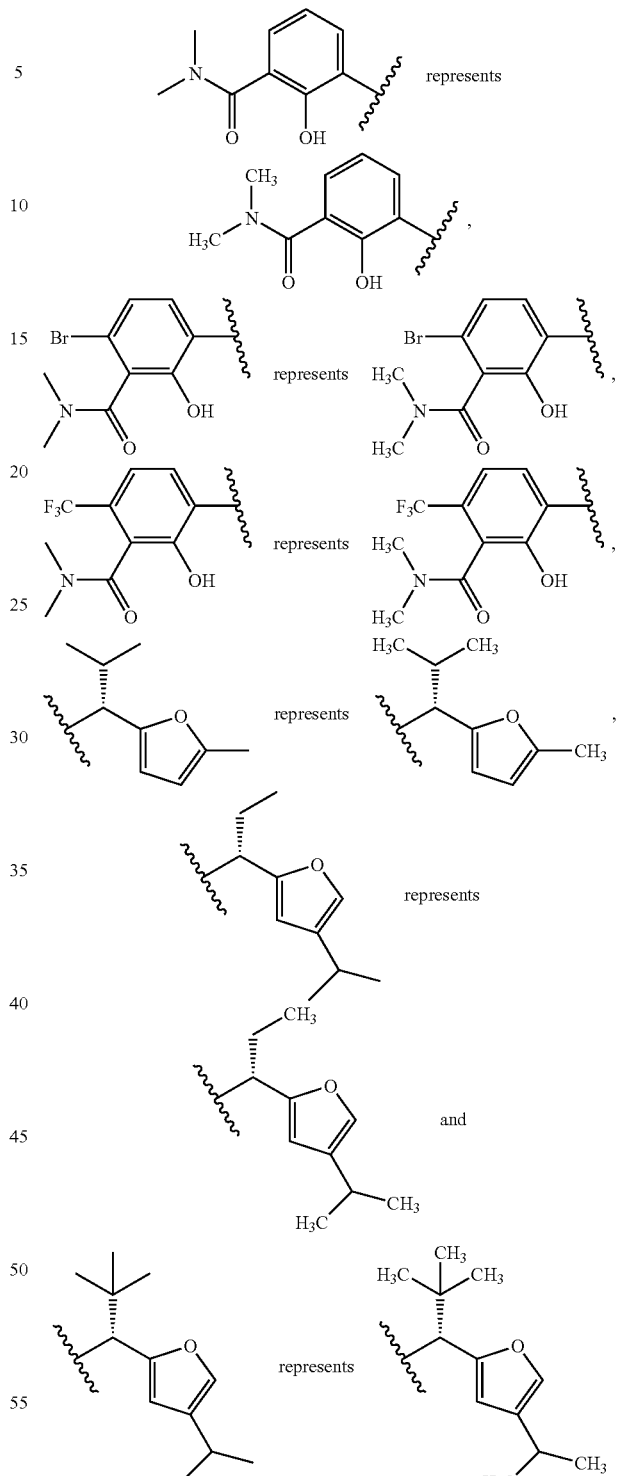

It should also be noted that throughout the specification and claims appended hereto, that any formula, compound, moiety or chemical illustration with unsatisfied valences is assumed to have the hydrogen atom to satisfy the valences unless the context indicates a bond.

The term "substituted" means substitution with specified groups other than hydrogen, or with one or more groups, moieties or radicals which can be the same or different, with each, for example, being independently selected.

The term "optionally substituted" means optional substitution with specified groups other than hydrogen, or with one or more groups, moieties or radicals which can be the same or different, with each, for example, being independently selected.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

The wavy line ∿∿ as a bond generally indicates a mixture of, or either of, the possible isomers, e.g., containing (R)- and (S)-stereochemistry. For example,

means containing both

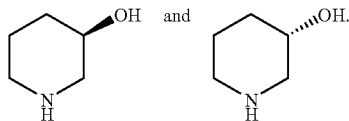

When the stereochemistry in a structure is not expressly indicated, the structure can have a mixture of, or any of the individual possible stereoisomers.

Lines drawn into the ring systems, such as, for example:

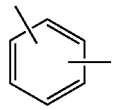

indicate that the indicated line (bond) may be attached to any of the substitutable ring carbon atoms.

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule is $H_2O$.

"Effective amount" or "therapeutically effective amount" is meant to describe an amount of compound or a composition of the present invention effective in antagonizing the neurokinin-1 receptor and thus producing the desired therapeutic effect in a suitable patient.

The compounds of Formula 1 form salts that are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates), undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g.

dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331, each of which is incorporated herein by reference.

All such acid salts and base salts are intended to be pharmaceutically acceptable salts within the scope of the invention and all acid and base salts are considered equivalent to the free forms of the corresponding compounds for purposes of the invention.

Compounds of Formula 1 and salts, solvates and prodrugs thereof, may exist in their tautomeric form (for example, as an amide or imino ether). All such tautomeric forms are contemplated herein as part of the present invention.

Polymorphic forms of the compounds of Formula 1, and of the salts, solvates, and/or prodrugs thereof, are intended to be included in the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds. "At least one", examples include 1-3, 1-2 or 1.

Compounds of Formula 1 are effective antagonists of the $NK_1$ receptor, and have an effect on its endogenous agonist, Substance P, at the $NK_1$ receptor site, and therefore, can be useful in treating diseases, disorders, or conditions caused or aggravated by the activity of the receptor.

The in vitro and in vivo $NK_1$, $NK_2$ and $NK_3$ activities of the compounds of Formula 1 can be determined by various procedures known in the art, such as a test for their ability to inhibit the activity of the $NK_1$ agonist Substance P. The percent inhibition of neurokinin agonist activity is the difference between the percent of maximum specific binding ("MSB") and 100%. The percent of MSB is defined by the following equation, wherein "dpm" represents "disintegrations per minute":

$$\% \ MSB = \frac{(\text{dpm of unknown}) - (\text{dpm on nonspecific binding})}{(\text{dpm of total binding}) - (\text{dpm of nonspecifc binding})} \times 100.$$

The concentration at which the compound produces 50% inhibition of binding is then used to determine an inhibition constant ("$K_i$") using the Chang-Prusoff equation.

In vivo activity may be measured by inhibition of an agonist-induced foot tapping in a gerbil, as described in *Science*, 281, 1640-1695 (1998), which is herein incorporated by reference in its entirety. It will be recognized that compounds of Formula 1 can exhibit $NK_1$ antagonist activities of varying degrees. For instance, certain compounds can exhibit stronger $NK_1$ antagonist activities than others.

The compounds of the present invention exhibit potent affinities for the $NK_1$ receptor as measured by $K_i$ values (in nM). The activities (potencies) for the compounds of the invention are determined by measuring their $K_i$ values. The smaller the $K_i$ value, the more active is a compound for antagonizing the $NK_1$ receptor. Compounds of the invention exhibit a wide range of activities. The $NK_1$ average $K_i$ values for compounds of Formula 1 generally range from 0.01 nM to about 1000 nM, preferably, from about 0.01 nM to about 500 nM, with values of from about 0.01 nM to about 100 nM being more preferred. Even more preferred are compounds having average $K_i$ values of from 0.01 nM to about 10 nM for the $NK_1$ receptor. Especially preferred compounds have $NK_1$ average $K_i$ values of from 0.01 nM to about 3 nM. Even more especially preferred compounds have $NK_1$ average $K_i$ values of from 0.01 nM to about 0.3 nM. Compounds 1a, 4a, 4b, 5a, 6a, 7, 8 and 9a (see examples, below) have $K_i$ values, respectively, of 0.23, 0.62, 0.32, 0.23, 0.14, 0.3, 0.36, and 0.28 nM.

Compounds of the Formula 1 have a number of utilities. For instance, the inventive compounds can be useful as antagonists of neurokinin receptors, particularly, $NK_1$ receptors in a mammal, such as a human. As such, they may be useful in treating and preventing one or more of a variety of mammalian (human and animal) disease states (physiological disorders, symptoms and diseases) in a patient in need of such treatment, wherein the disease states are selected from the group consisting of: (1) respiratory diseases (e.g., chronic lung disease, bronchitis, pneumonia, asthma, allergy, cough and bronchospasm), (2) inflammatory diseases (e.g., arthritis and psoriasis), (3) skin disorders (e.g., atopic dermatitis and contact dermatitis), (4) ophthalmologic disorders (e.g., retinitis, ocular hypertension and cataracts), (5) central nervous system conditions, such as depressions (e.g., neurotic depression), anxieties (e.g., general anxiety, social anxiety and panic anxiety disorders), phobias (e.g., social phobia), and bipolar disorder, (6) addictions (e.g., alcohol dependence and psychoactive substance abuse), (7) epilepsy, (8) nociception, (9) psychosis, (10) schizophrenia, (11) Alzheimer's disease, (12) AIDs related dementia, (13) Towne's disease, (14) stress related disorders (e.g., post traumatic stress disorder), (15) obsessive/compulsive disorders, (16) eating disorders (e.g., bulimia, anorexia nervosa and binge eating), (17) sleep disorders, (18) mania, (19) premenstrual syndrome, (20) gastrointestinal disorders (e.g., irritable bowel syndrome, Crohn's disease, colitis, and emesis), (21) atherosclerosis, (22) fibrosing disorders (e.g., pulmonary fibrosis), (23) obesity, (24) Type II diabetes, (25) pain related disorders (e.g., headaches, such as migraines, neuropathic pain, post-operative pain, and chronic pain syndromes), (26) bladder and genitourinary disorders (e.g., interstitial cystitis and urinary incontinence), (27) emesis (e.g., chemotherapy-induced (e.g., induced by cisplatin, doxorubicin, and taxane), radiation-induced, motion sickness, ethanol-induced, and post operative nausea and vomiting), and (28) nausea. Preferably, the inventive compounds can be useful in treating and preventing one of the following mammalian (e.g., human) disease states in a patient in need of such treatment: respiratory diseases (e.g., cough), depression, anxiety, phobia, and bipolar disorder, alcohol dependence, psychoactive substance abuse, nociception, psychosis, schizophrenia, stress related disorders, obsessive/compulsive disorder, bulimia, anorexia nervosa and binge eating, sleep disorders, mania, premenstrual syndrome, gastrointestinal disorders, obesity, pain related disorders, bladder disorders, genitourinary disorders, emesis and nausea. In particular, the compounds according to Formula 1 are useful for treating disease states related to microvascular leakage and mucus secretion. Consequently, the compounds of the invention are especially useful in the treatment and prevention of asthma, emesis, nausea, depressions, anxieties, cough and pain related disorders, more especially, emesis, depression, anxiety and cough.

In another aspect, the invention relates to pharmaceutical compositions comprising at least one compound (e.g., one to three compounds, preferably, one compound) represented by Formula 1 and at least one pharmaceutically acceptable excipient or carrier. The invention also relates to the use of such pharmaceutical compositions in the treatment of mammalian (e.g., human) disease states, such as those listed above.

In still another aspect of the invention, a method is provided for antagonizing the effects of a Substance P at a neurokinin-1 receptor site or for the blockade of one or more neurokinin-1 receptors in a mammal (i.e., a patient, e.g., a human) in need of such treatment, comprising administering to the mammal an effective amount of at least one (e.g., one) compound according to Formula 1.

In another aspect of the invention, an effective amount of one or more of the inventive $NK_1$ receptor antagonists may be combined with an effective amount of one or more anti-depressant agents and/or one or more anti-anxiety agents (e.g., gepirone, gepirone hydrochloride, nefazodone, and nefazodone hydrochloride (e.g., Serzone®)) to treat depression and/or anxiety. U.S. Pat. No. 6,117,855 (2000), the disclosure of which is incorporated herein by reference, discloses a method for treating or preventing depression or anxiety with a combination therapy of a specific $NK_1$ receptor antagonist together with an anti-depressant and/or anti-anxiety agent. Thus, anti-depressant and/or anti-anxiety agents, such as those disclosed in U.S. Pat. No. 6,117,855 (2000), can be combined with one or more (e.g., one) compounds of the Formula 1 to treat depression and/or anxiety disease states in a mammal, preferably, a human.

In still another aspect of the invention, an effective amount of one or more (e.g., one) of the inventive $NK_1$ receptor antagonists may be combined with an effective amount of one or more (e.g., one) selective serotonin reuptake inhibitors ("SSRIs") to treat a variety of mammalian disease states, such as those described above. SSRIs alter the synaptic availability of serotonin through their inhibition of presynaptic reaccumulation of neuronally released serotonin. U.S. Pat. No. 6,162,805 (2000), the disclosure of which is incorporated herein by reference, discloses a method for treating obesity with a combination therapy of a $NK_1$ receptor antagonist and an SSRI. One or more inventive compound(s) of the Formula 1 can be combined together with an SSRI(s) in a single pharmaceutical composition, or it can be administered simultaneously, concurrently or sequentially with an SSRI. This combination may be useful in the treatment and prevention of obesity or another of the above-identified human and animal disease states. In particular, an effective amount of at least one (e.g., one) compound having the Formula 1, alone or together with an effective amount of at least one (e.g., one) selective serotonin reuptake inhibitor, can be useful in the treatment and prevention of depression, and/or anxiety.

Numerous chemical substances are known to alter the synaptic availability of serotonin through their inhibition of presynaptic reaccumulation of neuronally released serotonin. Representative SSRIs include, without limitation, the following: fluoxetine, fluoxetine hydrochloride (e.g., Prozac®), fluvoxamine, fluvoxamine maleate (e.g. Luvox®), paroxetine, paroxetine hydrochloride (e.g., Paxil®), sertraline, sertraline hydrochloride (e.g., Zoloft®), citalopram, citalopram hydrobromide (e.g., Celexa™), duloxetine, duloxetine hydrochloride, venlafaxine, and venlafaxine hydrochloride (e.g., Effexor®). Further SSRIs include those disclosed in U.S. Pat. No. 6,162,805 (2000). Other compounds can readily be evaluated to determine their ability to selectively inhibit serotonin reuptake. Thus, one aspect of the invention relates to a pharmaceutical composition comprising at least one (e.g., one) $NK_1$ receptor antagonist having the Formula 1, at least one (e.g., one) SSRI, and at least one pharmaceutically acceptable excipient or carrier. Another aspect of the invention relates to a method of treating the above identified mammalian (e.g., human) disease states, the method comprising administering to a patient in need of such treatment an effective amount of a pharmaceutical composition comprising at least one (e.g., one) $NK_1$ receptor antagonist having the Formula 1 in combination with at least one (e.g., one) SSRI, such as one of those recited above, and at least one pharmaceutically acceptable excipient or carrier.

In a preferred aspect, the invention relates to a method of treating depression and anxiety, the method comprising administering to a patient in need of such treatment an effective amount of at least one (e.g., one) $NK_1$ receptor antagonist having the Formula 1 in combination with at least one (e.g., one) SSRI, such as one of those described above. When an inventive $NK_1$ receptor antagonist is combined with an SSRI for administration to a patient in need of such treatment, the two active ingredients can be administered simultaneously, consecutively (one after the other within a relatively short period of time), or sequentially (first one and then the other over a period of time). In general, when the two active ingredients are administered consecutively or sequentially, the inventive $NK_1$ receptor antagonist is, preferably, administered before the administration of the SSRI.

It is another embodiment of the invention to treat a patient suffering from multiple ailments with a combination therapy, the therapy comprising administering to a patient (e.g., a mammal, preferably a human) in need of such treatment at least one compound of Formula 1, and at least one other active ingredient (i.e., drug) used for treating one or more of the ailments being suffered by the patient. The compounds of Formula 1 and the other active ingredients can be administered sequentially, concurrently and/or simultaneously. The compounds of Formula 1 and the other active ingredients can be administered separately in any suitable dosage form. Preferably, administration is accomplished using an oral dosage forms or using a transdermal patches. The compounds of Formula 1 and the other active ingredients can be formulated together and administered in one combined dosage form.

Thus, the compounds of the invention may be employed alone or in combination with other active agents. Combination therapy includes the administration of two or more active ingredients to a patient in need of treatment. In addition to the above described NK$_1$ receptor antagonist/SSRI combination therapy, the compounds having the Formula 1 may be combined with one or more other active agents, such as the following: other types of NK$_1$ receptor antagonists (e.g., those that are disclosed in neurokinin receptor antagonist patents cited above), prostanoids, H$_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, ETA antagonists, renin inhibitors, serotonin 5-HT$_3$ receptor antagonists (e.g., ondansetron, ondansetron hydrochloride (e.g., Zolfran®), palonosetron, granisetron, and granisetron hydrochloride (e.g., Kytril®), serotonin 5-HT$_{2c}$ receptor agonists, nociceptin receptor agonists, glucocorticoids (e.g., dexamethasone), rho kinase inhibitors, potassium channel modulators and/or inhibitors of multi-drug resistance protein 5.

Preferable therapeutic agents for combination therapy with compounds of the invention are the following: prostanoids, such as prostaglandin E$_1$; α-adrenergic agonists, such as phentolamine mesylate; dopamine receptor agonists, such as apomorphine; angiotensin 11 antagonists, such as losartan, irbesartan, valsartan and candesartan; ET$_A$ antagonists, such as bosentan and ABT-627; serotonin 5-HT$_3$ receptor antagonists, such as ondansetron; and glucocorticoids, such as dexamethasone. In preferred embodiments of the invention, the inventive compounds can be combined with: other types of NK$_1$ receptor antagonists, SSRIs, dopamine receptor agonists, serotonin 5-HT$_3$ receptor antagonists, serotonin 5-HT$_{2c}$ receptor agonists, nociceptin receptor agonists, glucocorticoids and/or inhibitors of multi-drug resistance protein 5.

A preferred embodiment of the invention is directed to a method of treating emesis and/or nausea in a patient in need of such treatment using a combination therapy comprising administering to the patient an effective amount of at least one (e.g., one) compound having the Formula 1 in combination with an effective amount of at least one (e.g., one) serotonin 5-HT$_3$ receptor antagonist (e.g., ondansetron) and/or at least one (e.g., one) glucocorticoid (e.g., dexamethasone). Preferably, the compound of Formula 1 is administered orally or by IV.

Another embodiment of this invention is directed to a method for treating a physiological disorder, symptom or disease in a patient in need of such treatment, comprising administering to the patient an effective amount of at least one compound of Formula 1, and an effective amount of at least one active ingredient selected from the group consisting of: other NK$_1$ receptor antagonists, selective serotonin reuptake inhibitors, dopamine receptor agonists, serotonin 5-HT$_3$ receptor antagonists, serotonin 5-HT$_{2c}$ receptor agonists, nociceptin receptor agonists, glucocorticoids and inhibitors of multidrug resistance protein 5, wherein the physiological disorder, symptom or disease is selected from the group consisting of: a respiratory disease, depression, anxiety, phobia, bipolar disorder, alcohol dependence, psychoactive substance abuse, nociception, psychosis, schizophrenia, stress related disorder, obsessive/compulsive disorder, bulimia, anorexia nervosa, binge eating, sleep disorder, mania, premenstrual syndrome, gastrointestinal disorder, obesity, headache, neuropathic pain, post-operative pain, chronic pain syndrome, bladder disorder, genitourinary disorder, cough, emesis and nausea.

Another aspect of the invention is to provide a kit comprising, in separate containers in a single package, pharmaceutical compositions for use in combination to treat an NK$_1$ receptor mediated disease, wherein one container comprises a pharmaceutical composition comprising an effective amount of a compound of Formula 1 in a pharmaceutically acceptable carrier, and wherein, a separate container comprises a pharmaceutical composition comprising another therapeutic agent in a pharmaceutically acceptable carrier, the therapeutic agent being selected from the group consisting of: SSRIs, other types of NK$_1$ receptor antagonists, prostanoids, H$_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, ETA antagonists, renin inhibitors, serotonin 5-HT$_3$ receptor antagonists, serotonin 5-HT$_{2c}$ receptor agonists, nociceptin receptor agonists, glucocorticoids, rho kinase inhibitors, potassium channel modulators and inhibitors of multi-drug resistance protein 5.

Another aspect of the invention is to provide a kit comprising, in separate containers in a single package, pharmaceutical compositions for use in combination to treat depression and/or anxiety, wherein one container comprises a pharmaceutical composition comprising an effective amount of a compound of Formula 1 in a pharmaceutically acceptable carrier, and wherein, a separate container comprises a pharmaceutical composition comprising an antidepressant agent in a pharmaceutically acceptable carrier, and/or wherein a separate container comprises a pharmaceutical composition comprising an antianxiety agent in a pharmaceutically acceptable carrier.

Another aspect of the invention is to provide a kit comprising, in separate containers in a single package, pharmaceutical compositions for use in combination to treat an NK$_1$ receptor mediated disease, wherein one container comprises a pharmaceutical composition comprising an effective amount of a compound of Formula 1 in a pharmaceutically acceptable carrier, and wherein, a separate container comprises a pharmaceutical composition comprising an SSRI in a pharmaceutically acceptable carrier.

Another aspect of the invention is to provide a kit comprising, in separate containers in a single package, pharmaceutical compositions for use in combination to treat depression and/or anxiety, wherein one container comprises a pharmaceutical composition comprising an effective amount of a compound of Formula 1 in a pharmaceutically acceptable carrier, and wherein, a separate container comprises a pharmaceutical composition comprising an SSRI in a pharmaceutically acceptable carrier.

Another aspect of the invention is to provide a kit comprising, in separate containers in a single package, pharmaceutical compositions for use in combination to treat emesis and/or nausea, wherein one container comprises a pharmaceutical composition comprising an effective amount of a compound of Formula 1 in a pharmaceutically acceptable carrier, and wherein, a separate container comprises a pharmaceutical composition comprising a serotonin 5-HT$_3$ receptor antagonist in a pharmaceutically acceptable carrier, and/or wherein a separate container comprises a pharmaceutical composition comprising a glucocorticoid in a pharmaceutically acceptable carrier.

Another aspect of the invention is to provide a kit comprising, in separate containers in a single package, pharmaceutical compositions for use in combination to treat emesis and/or nausea, wherein one container comprises a pharmaceutical composition comprising an effective amount of a compound of Formula 1 in a pharmaceutically acceptable carrier, and wherein, a separate container comprises ondansetron, and/or wherein a separate container comprises dexamethasone.

Another aspect of the invention is to provide a kit comprising, in separate containers in a single package, pharmaceutical compositions for use in combination to treat an $NK_1$ receptor mediated disease, wherein one container comprises a pharmaceutical composition comprising an effective amount of a compound of Formula 1 in a pharmaceutically acceptable carrier, and wherein, a separate container comprises a pharmaceutical composition comprising a therapeutic agent in a pharmaceutically acceptable carrier, the therapeutic agent being selected from the group consisting of: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and inhibitors of multi-drug resistance protein 5.

Pharmaceutical compositions may contain from about 0.1 to about 99.9 weight percent, or from about 5 to about 95 weight percent, or from about 20 to about 80 weight percent of active ingredient (compound of the Formula 1). For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: *The Science and Practice of Pharmacy*, 20$^{th}$ Edition, (2000), Lippincott Williams & Wilkins, Baltimore, Md., herein incorporated by reference.

Liquid form preparations include solutions, suspensions and emulsions, for example, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 4000 mg, preferably from about 0.02 mg to about 1000 mg, more preferably from about 0.3 mg to about 500 mg, and most preferably from about 0.04 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.02 mg/day to about 2000 mg/day, in two to four divided doses.

The pharmaceutical compositions of the invention may be administered from about 1 to about 5 times per day, or alternatively, as a continuous infusion. Such administration can be used as a chronic or acute therapy.

The quantity of $NK_1$ receptor antagonist in combination with a selective serotonin reuptake inhibitor ("SSRI") in a unit dose of preparation may be from about 10 to about 300 mg of $NK_1$ receptor antagonist combined with from about 10 to about 100 mg of SSRI. In another combination the quantity of $NK_1$ receptor antagonist in combination with a SSRI in a unit dose of preparation may be from about 50 to about 300 mg of $NK_1$ receptor antagonist combined with from about 10 to about 100 mg of SSRI. In another combination the quantity of $NK_1$ receptor antagonist in combination with SSRI in a unit dose of preparation may be from about 50 to about 300 mg of $NK_1$ receptor antagonist combined with from about 20 to about 50 mg of SSRI.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art.

EXAMPLES

The invention disclosed herein is exemplified by the following preparations and examples, which should not be construed to limit the scope of the disclosure. Alternative mechanistic pathways and analogous structures may be apparent to those skilled in the art.

Compounds 1-4 shown below may be prepared by the methods described in WO03/051840 (i.e., compounds 23, 46, 45, and 42, respectively). WO03/051840 is herein incorporated by reference.

compound 1

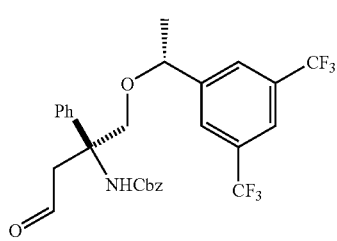

compound 2

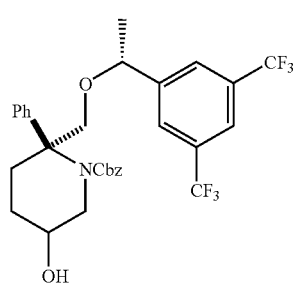

compound 3

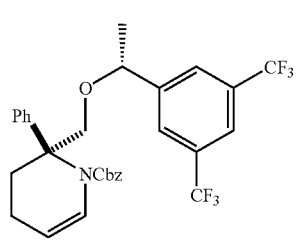

compound 4

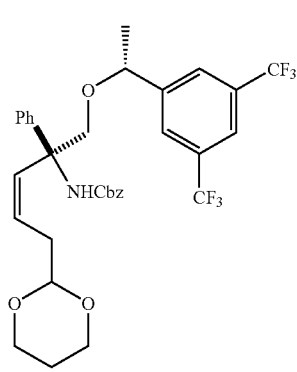

Preparative Example 1

Example 1a

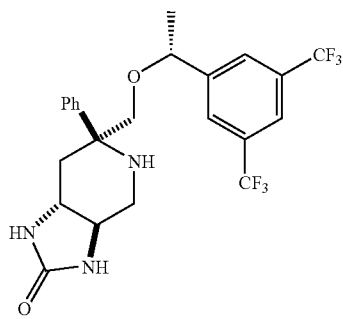

Example 1b

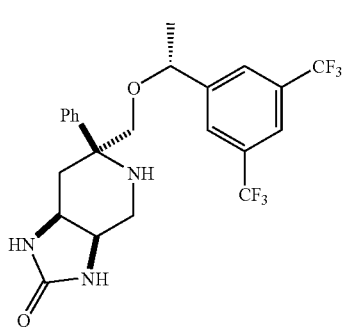

Example 1c

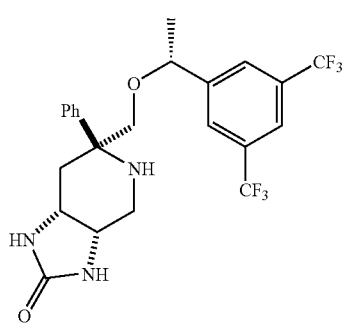

Example 1d

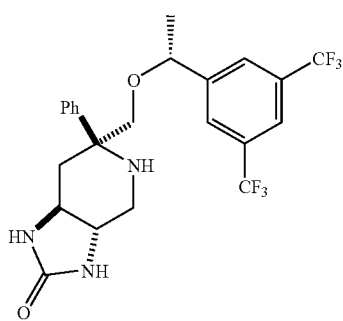

Step A:

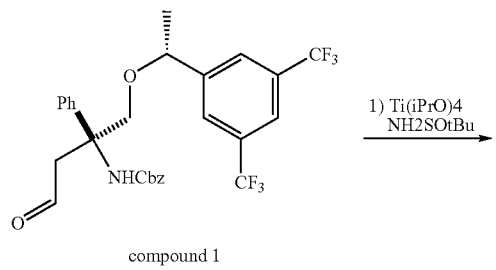

compound 1

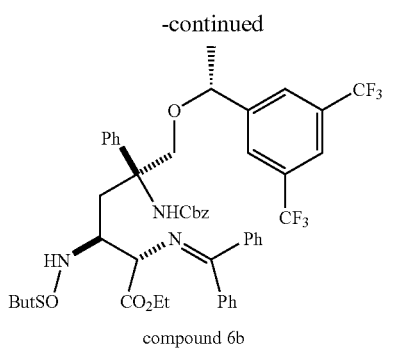

compound 6b

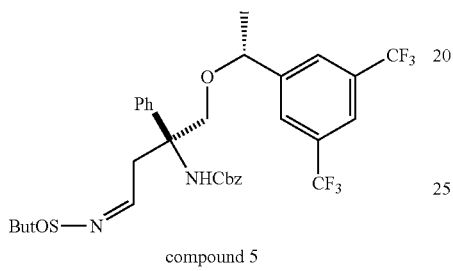

compound 5

Compound 1 (13.13 g, 23.7 mmol) was dissolved in 40 mL of anhydrous $CH_2Cl_2$ and maintained under a $N_2$ atmosphere. (R)-t-butylsulfinamide (3.0 g, 23.7 mmol) was then added, followed by the addition of 13.7 mL of $Ti(iPrO)_4$. The resulting solution was stirred for 18 h. Under vigorous stirring, 100 mL of EtOAc and 100 mL of brine was added to the solution. The resulting suspension was filtered through a pad of Celite (i.e., diatomaceous earth) and the Celite was washed three times with 100 mL of EtOAc. The combined filtrate was separated from the water layer. The organic layer was dried with $Na_2SO_4$, filtered and concentrated to give 10.9 g (70%) of compound 5 as a light yellow oil.

Step B:

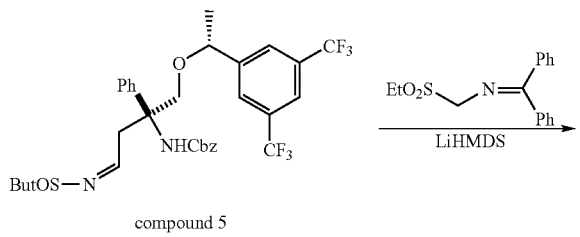

compound 5

N-(diphenylmethylene)glycine ethyl ester was dissolved in 15 mL of THF and maintained under a $N_2$ atmosphere at 0° C. LiHMDS (1.0M in THF, 5.3 mL) was added, and the resulting solution was stirred for 5 min. A solution of compound 5 (1.16 g, 1.78 mmol) in 5 mL anhydrous THF was then cannulated into above enolate solution. After 1 h at 0° C., the reaction mixture was quenched by the addition of 10 mL saturated $NH_4Cl$ solution. The resulting organic and aqueous phases were separated and the aqueous phase was extracted three times with 10 mL of EtOAc. The organic phases were combined and washed with a saturated $NaHCO_3$ solution, then a brine solution. The washed organic phase was then dried and concentrated. After purification by silica gel flash chromatography (eluent: 20% EtOAc/Hexanes), three isomers were obtained: compounds 6a, 6b and 6c.

Step C:

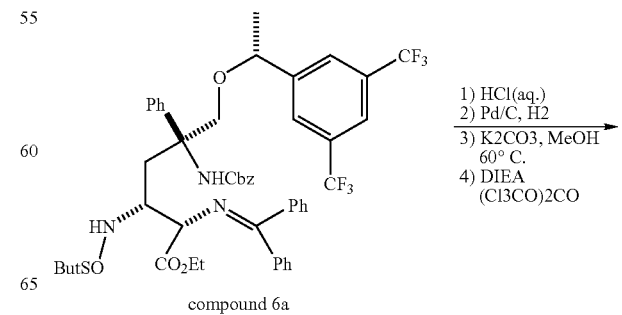

compound 6a

1) HCl(aq.)
2) Pd/C, $H_2$
3) $K_2CO_3$, MeOH 60° C.
4) DIEA $(Cl_3CO)_2CO$

-continued

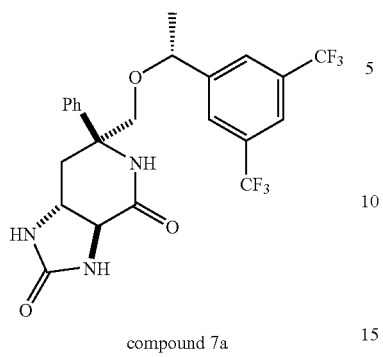

compound 7a

A solution of compound 6a (230 mg, 0.25 mmol) in absolute MeOH (2.5 mL) was treated with 2N HCl solution (2.5 mL), and stirred at 23° C. for 18 h. The reaction mixture was diluted with Et$_2$O, and made basic by adding a 2N NaOH solution until a pH of 12 was obtained. The resulting aqueous and organic phases were separated. The aqueous phase was extracted three times with 10 mL of Et$_2$O. The organic phases were combined, and then dried with anhydrous K$_2$CO$_3$ and concentrated. The resulting residue was dissolved in 3 mL of EtOH and 0.05 mL of 1,4-cyclohexadiene, to which Pd on carbon (10%, 100 mg) was added. The resulting suspension was heated at 80° C. for 1 h. The suspension was filtered through Celite and concentrated. The resulting residue was dissolved in 2.5 mL of CH$_2$Cl$_2$ to which 0.5 mL of DIEA and triphosgene (36 mg, 0.12 mmol) was added. The mixture was stirred for 1 h, and then partitioned between 10 mL of EtOAc and 10 mL of 1N HCl solution. The resulting organic phase was washed sequentially with a NaHCO$_3$ solution and a brine solution, then dried and concentrated. The resulting concentrate was purified by preparative TLC (silica gel; 5% methanol/CH$_2$Cl$_2$), to give compound 7a as a product (electrospray MS [M+1]$^+$ 487.1).

A similar procedure was used to convert compounds 6b and 6c to compounds 7b and 7c (electrospray MS [M+1]$^+$ compound 6b: 487; compound 6c: 487.1).

Step D:

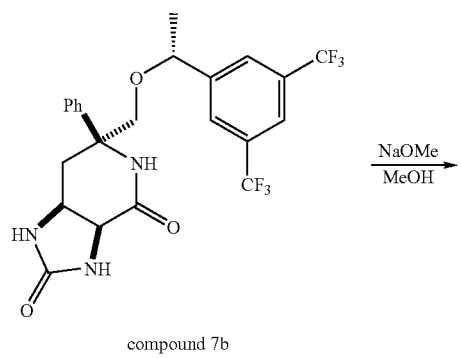

compound 7b

-continued

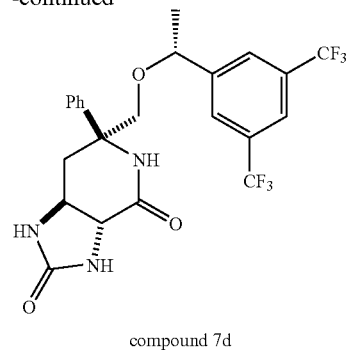

compound 7d

A solution of compound 7b (90 mg, 0.06 mmol) in MeOH (2 mL) was treated with 0.2 mL of 30% NaOMe in MeOH and stirred overnight. The reaction mixture was quenched by the addition of 4 drops of 4 N HCl in dioxane, and then the solution was concentrated under reduced pressure. The residue was purified using preparative TLC (silica gel; 5% methanol/CH$_2$Cl$_2$) to give compound 7d.

Step E:

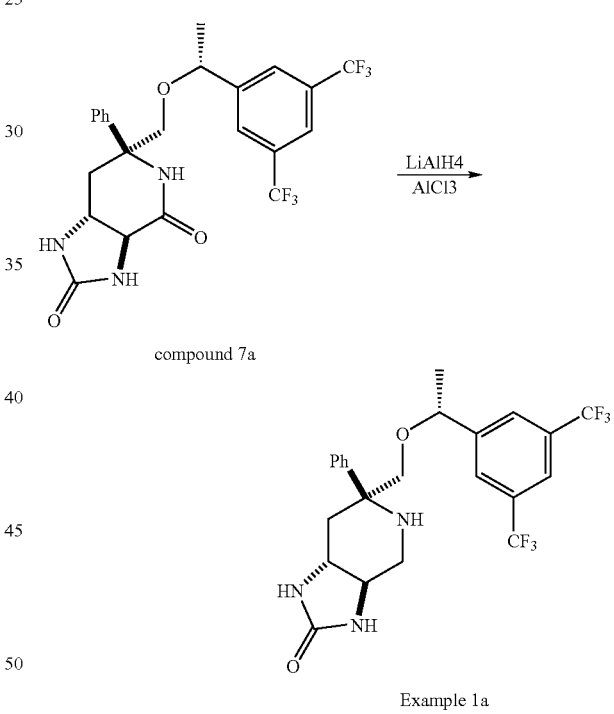

Example 1a

LiAlH$_4$ (1M in Et$_2$O, 0.268 mL) was added to AlCl$_3$ (solid) at 0° C., and the mixture was stirred for 10 min. Then a solution of compound 7a in 1 mL THF was cannulated into the mixture. The reaction mixture was allowed to warm to 23° C. and stirring was continued for 5 h. The mixture was then diluted with 10 mL of THF. 5 mL of Na,K tartrate solution was then added carefully and the mixture was stirred overnight. The resulting organic and aqueous phases were separated, and the aqueous phase was extracted five times with 15 mL of EtOAc. The organic phases where combined, then washed with brine, dried and concentrated. The resulting residue was purified using preparative TLC (silica gel; 5% methanol/CH$_2$Cl$_2$) to give Example 1a (electrospray MS [M+1]$^+$ 488.1).

A similar procedure was used to convert compounds 7b-7d to Examples 1b-1d (electrospray MS [M+1]+ compound 1b: 488.1; compound 1c: 488.1; compound 1d: 488.1).

Preparative Example 2

Example 2

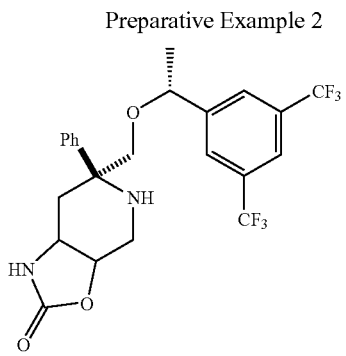

Step A:

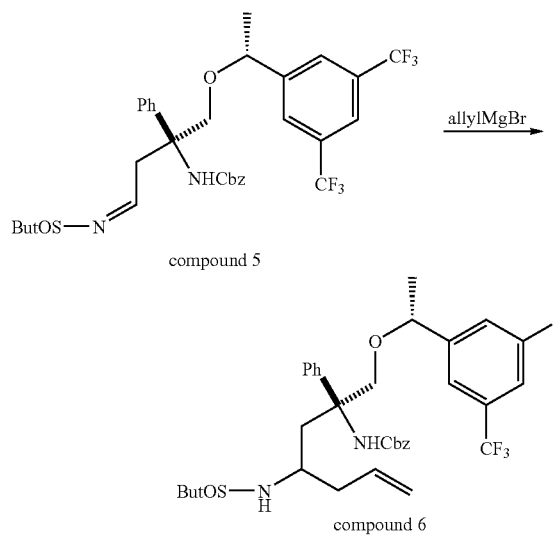

Compound 5 (2.0 g, 3.05 mmol) was dissolved in 15 mL of CH$_2$Cl$_2$ and maintained at −78° C. AllylMgBr (1M in Et$_2$O, 9.1 mmol) was added, and the solution was allowed to warm to 23° C. overnight. The reaction mixture was quenched with a NH$_4$Cl solution and extracted with EtOAc. The resulting organic phase was washed with brine, dried, and was concentrated. The crude product was purified by flash chromatography (silica gel; 5-20% EtOAc/hexane) to give compound 6.

Step B:

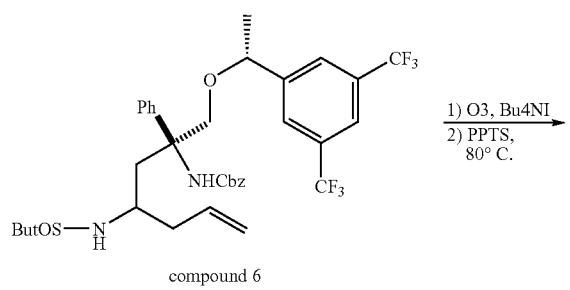

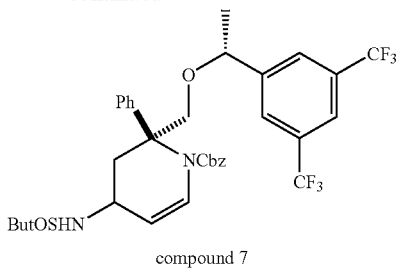

Compound 6 (430 mg, 0.62 mmol) was dissolved in 2 mL of CH$_2$Cl$_2$ and cooled to −78° C. Ozone was bubbled into the solution for 20 min, then a stream of nitrogen was introduced into the reaction mixture until the solution became colorless. The solution was then treated with tetrabutylammonium iodide (457.3 mg, 1.24 mmol) and stirred overnight. The solution was concentrated, and the resulting residue was dissolved in 2 mL of toluene. About 2 crystals of pyridinium p-toluenesulfonic acid were then added and the solution was heated at 80° C. for 30 min. The solution was loaded onto a silica gel column and eluted with 2%-5% EtOAc/Hexanes to give compound 7.

Step C:

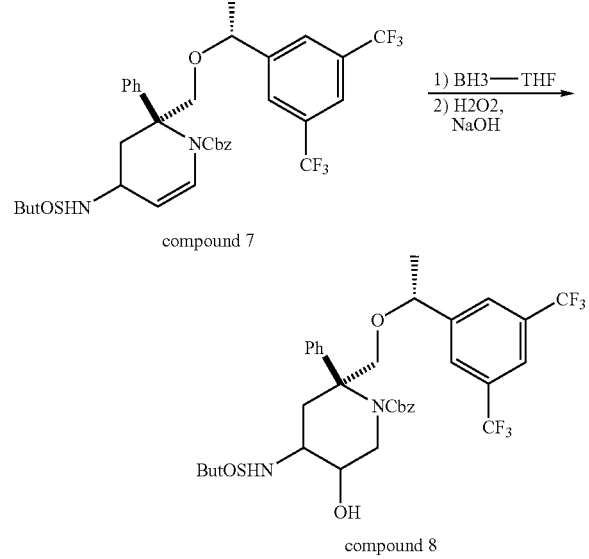

Compound 7 (120 mg, 0.176 mmol) was dissolved in 2 mL of THF, and cooled to 0° C. A solution of BH$_3$-Me$_2$S in THF (264 mL, 2.0M solution; 0.528 mmol) was added and the resulting reaction mixture was stirred overnight at 23° C. The reaction mixture was quenched by diluting it with 2 mL of THF followed by the addition of 2 mL of 2N NaOH and 2 mL of 30% H$_2$O$_2$, then stirred for 6 h. The organic and aqueous phases were separated, and the aqueous phase was extracted three times with 10 mL of Et$_2$O. The combined organic phases were dried and concentrated. The resulting residue was purified using preparative TLC (silica gel; 2:1 EtOAc/hexane) to give the product, compound 8.

Step D:

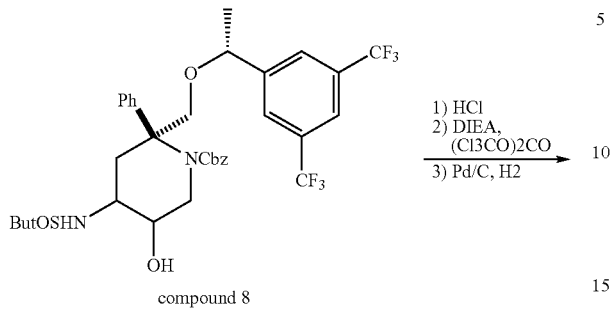
compound 8

1) HCl
2) DIEA, (Cl3CO)2CO
3) Pd/C, H2

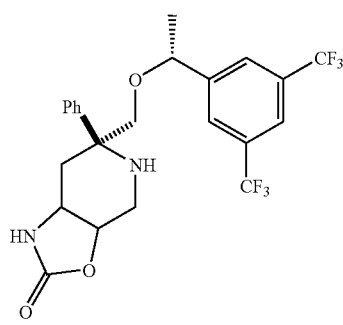
Example 2

Compound 8 (30 mg, 0.043 mmol) was dissolved in 0.5 mL of MeOH, and maintained at 0° C. HCl (4N in dioxane, 0.5 mL) was added and the mixture was stirred at 23° C. for 2 h. The solvents were removed and the resulting residue was dissolved in 2 mL of CH$_2$Cl$_2$ and cooled to 0° C. DIEA (0.1 mL) and triphosgene (6.4 mg, 0.021 mmol) were then added, and the solution was stirred for 2 h, was subsequently passed through a pad of silica gel and washed with 50% EtOAc. The eluent was concentrated and the resulting residue was dissolved in 2 mL of MeOH. Pd/C (10% Pd on carbon, 4.6 mg) and 0.5 mL of 1,4-cyclohexadiene were then added. The resulting mixture was heated for 20 min, then filtered through a pad of Celite, concentrated and applied to a prep TLC plate (silica gel), and eluted with 50% EtOAc/hexanes to provide Example 2 (electrospray MS [M+1]$^+$ 489.1).

Preparative Example 3

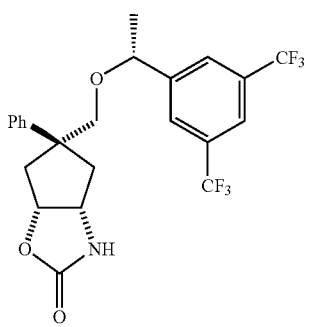
Example 3a

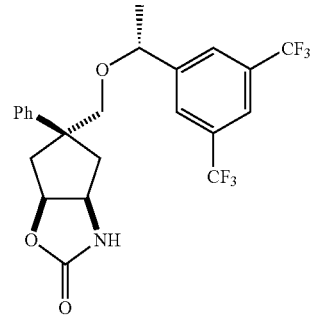
Example 3b

Step A:

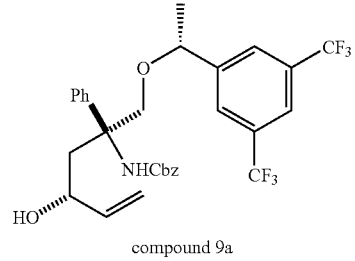
compound 1

BF3—Et2O
/MgBr

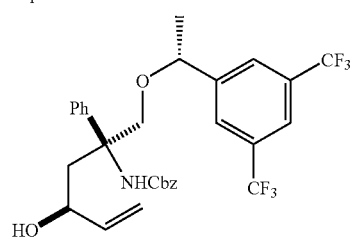
compound 9a compound 9b

Compound 1 (3.0 g, 5.4 mmol) was dissolved in 27 mL of THF, and maintained at 0° C. BF$_3$-Et$_2$O (755 μl, 6.0 mmol) was added, and the mixture was stirred for 10 min. Vinyl magnesium bromide (1.0M in THF, 16.2 mL, 16.2 mmol) was added rapidly, and the reaction mixture was stirred at 0° C. for 2 h. The reaction mixture was then quenched with a NH$_4$Cl solution. The organic phase was separated, dried and concentrated. The resulting crude product was purified by column chromatography (silica gel) using 5% EtOAc in 1:1 Hexane/CH$_2$Cl$_2$ as the eluent, to give two isomers of compounds 9a and 9b.

Step B:

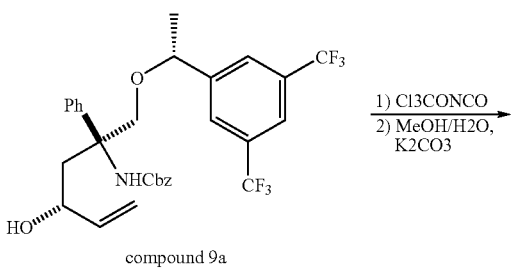

compound 9a

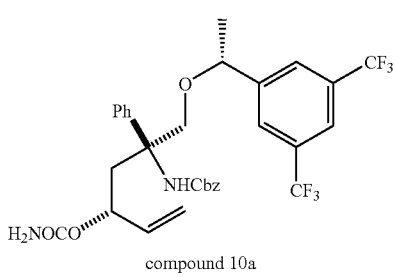

compound 10a

Compound 9a (380 mg, 0.65 mmol) was dissolved in 6.5 mL of CH₂Cl₂ and the resulting solution was maintained at 0° C. Cl₃CC(O)NCO (0.094 mL, 0.784 mmol) was then added, and the solution was stirred for 2 h. Another portion of Cl₃CC(O)NCO (0.045 mL, 0.35 mmol) was added, and the reaction mixture was allowed to warm to 23° C. After 1 h, the reaction mixture was concentrated and the resulting residue was dissolved in 9 mL of MeOH and 1.5 mL of H₂O. Then 750 mg of K₂CO₃ was added, and the mixture was stirred at 23° C. for 1 h. The solvent was then removed and the mixture was partitioned between EtOAc and H₂O. The aqueous phase was extracted three times with 10 mL of EtOAc. The combined organic phases were then dried and concentrated. Column chromatography (silica gel; 5% EtOAc in 1:1 hexane/CH₂Cl₂) of the crude product afforded compound 10a.

Step C:

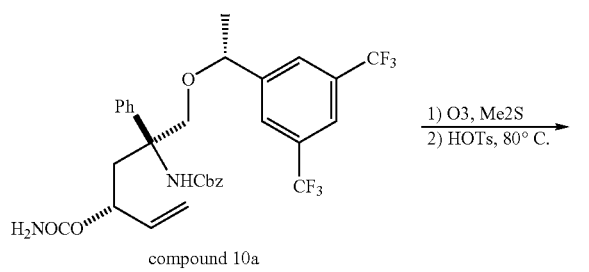

compound 10a

-continued

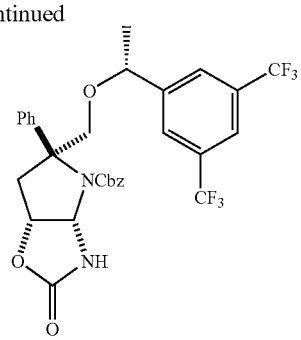

compound 11a

Compound 10a (140 mg, 0.224 mmol) was dissolved in 1.5 mL of CH₂Cl₂ and cooled to −78° C. Ozone was then bubbled through the solution. After the solution turned light blue, nitrogen was introduced until the solution became colorless. The reaction mixture was treated with 1 mL of Me₂S, warmed up to 23° C. and stirred for 3 h. The solvent was then removed. The resulting residue was dissolved in 2 mL of toluene, and then 5 mg of p-toluenesulfonic acid was added and the solution was heated to 65-70° C. and maintained at that temperature overnight. The reaction mixture was then loaded onto a silica gel column and eluted with EtOAc to afford compound 11a.

Step D:

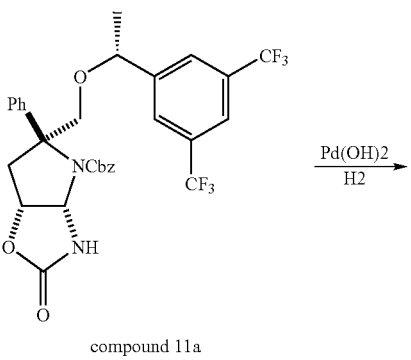

compound 11a

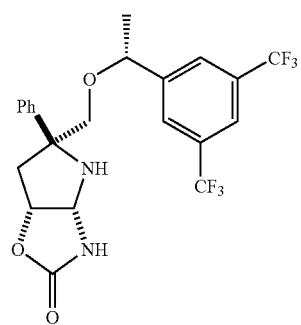

Example 3a

Compound 11a (47 mg, 0.077 mmol) was dissolved in 1 mL of EtOH. Pd(OH)₂/C (8 mg, 20% Pd) was added and a hydrogen balloon was attached to the flask holding the mixture. The hydrogenation was carried out overnight. The reaction mixture was then filtered and purified by preparative TLC (silica gel; EtOAc) to give Example 3a (electrospray MS [M+1]+475.1).

A similar procedure was used to convert compound 9b to Example 3b (electrospray MS [M+1]+475.1).

Preparative Example 4

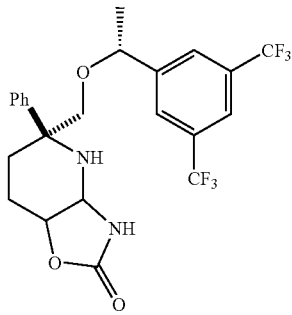

Example 4a and 4b

Step A:

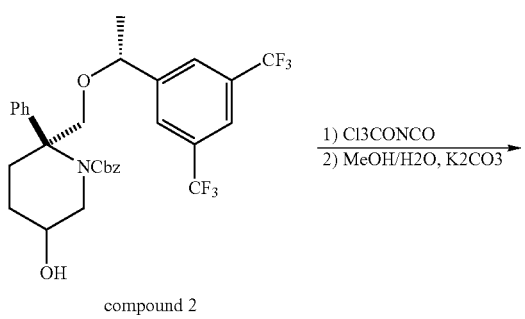

Following a procedure similar to that described in Example 3, step B, above, compound 2 was converted to the corresponding carbamate compound 12.

Step B:

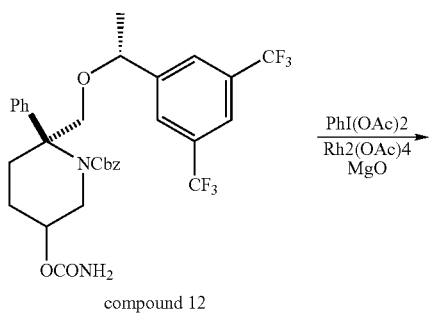

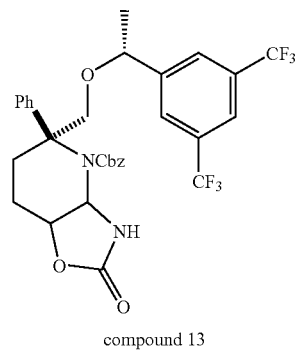

compound 13

Compound 12 (300 mg, 0.48 mmol) was dissolved in 4.8 mL of $CH_2Cl_2$ and was then treated with $PhI(OAc)_2$ (216.5 mg, 0.67 mmol), $Rh_2(OAc)_4$ (42 mg, 0.096 mmol) and MgO (44.5 mg, 1.1 mmol). The resulting mixture was heated at 40-46° C. for 24 h, then filtered through a pad of Celite 545, concentrated and purified using column chromatography (silica gel; 20-50% EtOAc/hexane), to give compound 13.

Step C:

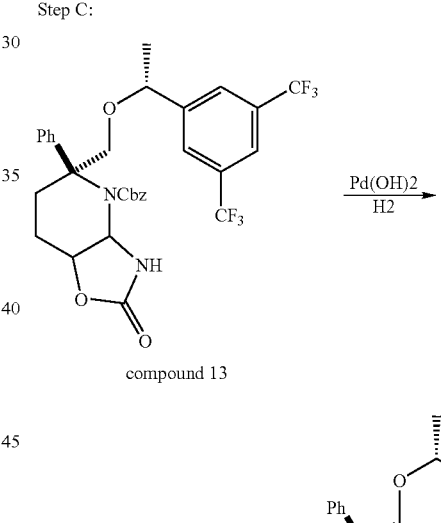

Example 4a and 4b

Compound 13 (185 mg, 0.3 mmol) was dissolved in 3 mL of EtOH. 20% $Pd(OH)_2$/C (25 mg) was added to the solution, and then hydrogenation was carried out overnight by affixing a hydrogen balloon to the reaction vessel. The reaction mixture was then filtered, concentrated, and purified using a HPLC OD column with an eluent of 1:9 iPA:hexanes. The first fraction of product Example 4a had a retention time of 80.6 min and a second isomer of the product, Example 4b had a retention time of 93.1 min (electrospray MS [M+1]+ Example 4a: 489.1; Example 4b: 489.1).

Preparative Example 5

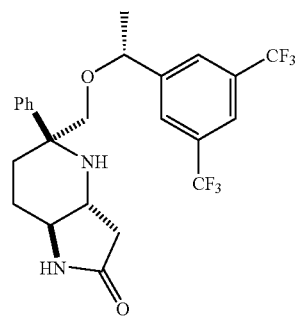

Example 5a

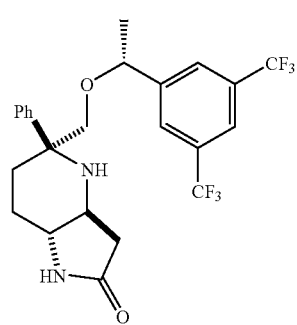

Example 5b

Method 1:

Step A:

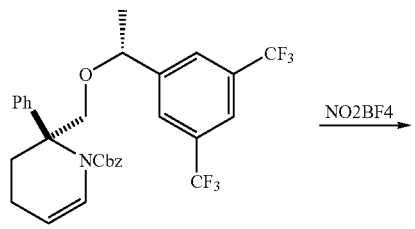

compound 3

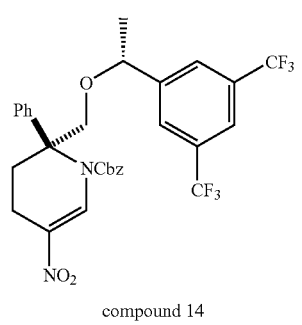

compound 14

Compound 3 (20.0 g, 35.5 mmol) was dissolved in 300 mL of THF and cooled to −30° C. NO$_2$BF$_4$ (9.5 g, 68.8 mmol) was then added in one portion. The solution was allowed to warm to 23° C. and stirred for 3 h. Then 200 mL of saturated NaHCO$_3$ solution was added, and the mixture was stirred for 30 min. The organic and aqueous phases were then separated.

The aqueous phase was extracted three times with 30 mL of Et$_2$O. The combined organic phases were dried and concentrated to give compound 14, which was used without further purification.

Step B:

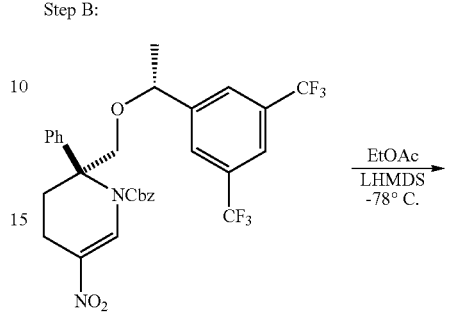

compound 14

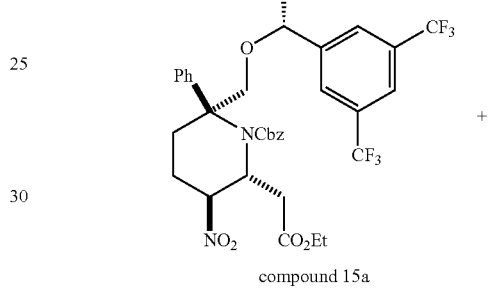

compound 15a

+

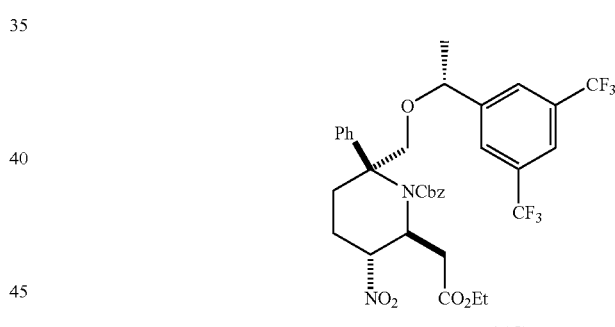

compound 15b

A 25 mL pear-shaped flask was charged with compound 14 (1.4 g, 2.30 mmol, 1.0 equiv.), anhydrous THF (9 mL), dry EtOAc (0.45 mL, 4.60 mmol, 2.0 equiv.) and DMPU (0.7 mL). The resulting brownish solution was cooled to −78° C. A 1.0M solution of LiHMDS in THF (4.6 mL, 4.60 mmol, 2.0 equiv.) was syringed dropwise into the flask. The solution was then stirred at −78° C. for 2 hours. The reaction mixture was quenched with saturated NH$_4$Cl solution at −78° C., and then allowed to warm up to room temperature. The mixture was diluted with diethyl ether, and then the organic and aqueous phases were separated. The aqueous phase was further extracted with diethyl ether. The combined organic phase was dried over anhydrous MgSO$_4$, filtered, and concentrated to provide a crude product. The crude product was purified in a silica column (10% to 15% EtOAc/hexane eluent) to afford compound 15a (eluted second) (562 mg, yield 35%) and compound 15b (eluted first) (300 mg, yield 18.8%).

Step C:

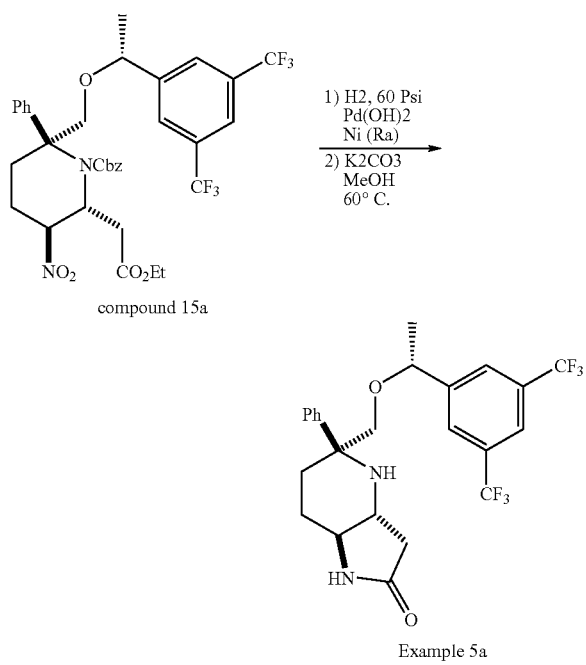

Example 5a

A 250 mL Parr shaker bottle was charged with compound 15a (300 mg, 0.44 mmol, 1.0 equiv.) and MeOH (10 mL). After dry nitrogen gas was bubbled through this reaction mixture, Pd(OH)$_2$/C (63 mg, 20% wt, 0.088 mmol, 0.2 equiv.) and an approximately equal volume of Raney Ni were added. The shaker bottle was then shaken under a hydrogen atmosphere (60 psi) for 48 hours. The reaction mixture was diluted with MeOH, and then carefully passed through a Celite packed funnel. The Celite pad was thoroughly washed with MeOH. The filtrate was treated with MeONa (25 mg, 0.46 mmol, 1.05 equiv.) and heated at 70° C. for 3 hours. TLC analysis (5% MeOH/CH$_2$Cl$_2$; silica gel) showed only one product. The mixture was concentrated to dryness and then re-dissolved in diethyl ether, washed with a saturated sodium bicarbonate solution, and then the organic and aqueous phases were separated. The aqueous phase was further extracted with diethyl ether. The combined organic phases were dried over anhydrous MgSO$_4$, filtered and concentrated to give the crude product, which was purified on a silica gel flash chromatography column (3% MeOH/CH$_2$Cl$_2$) to afford Example 5a (112 mg, yield 52%), electrospray MS [M+1]+ 487.1.

Similar procedures were used to convert compound 15b to Example 5b (electrospray MS [M+1]+487.1).

Method 2:

Step A:

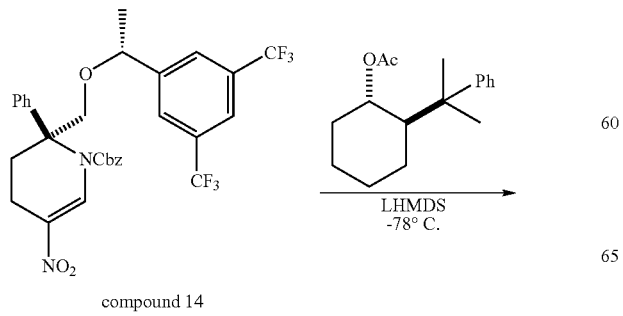

compound 14

To a mixture of compound 14 (145 mg, 0.238 mmol) and (1S,2R)-acetic acid 2-(1'-methyl-1'-phenyl-ethyl)-cyclohexyl ester (124 mg, 0.476 mmol) in anhydrous THF (2 mL) at −78° C. was added 1.0M solution of LiHMDS in THF (0.476 mL, 0.476 mmol) dropwise through a syringe. The solution was then stirred at −78° C. for 2 hours. The reaction mixture was quenched with a saturated NaHCO$_3$ solution at −78° C., and then allowed to warm up to room temperature, then stirred for 16 h. The mixture was diluted with EtOAc, and then the organic and aqueous phases were separated. The aqueous phase was further extracted with EtOAc. The combined organic phase was dried over anhydrous MgSO$_4$, filtered, and concentrated to provide a crude product. The crude product was purified in a silica column (10% to 15% EtOAc/hexane eluent) to afford compound 15c (135 mg, 65%).

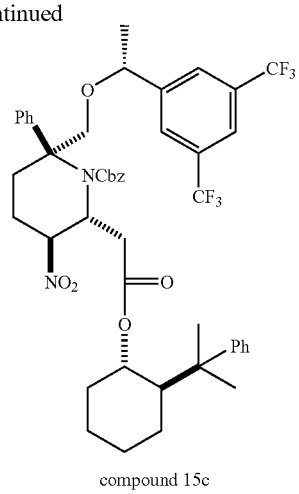

compound 15c

Step B:

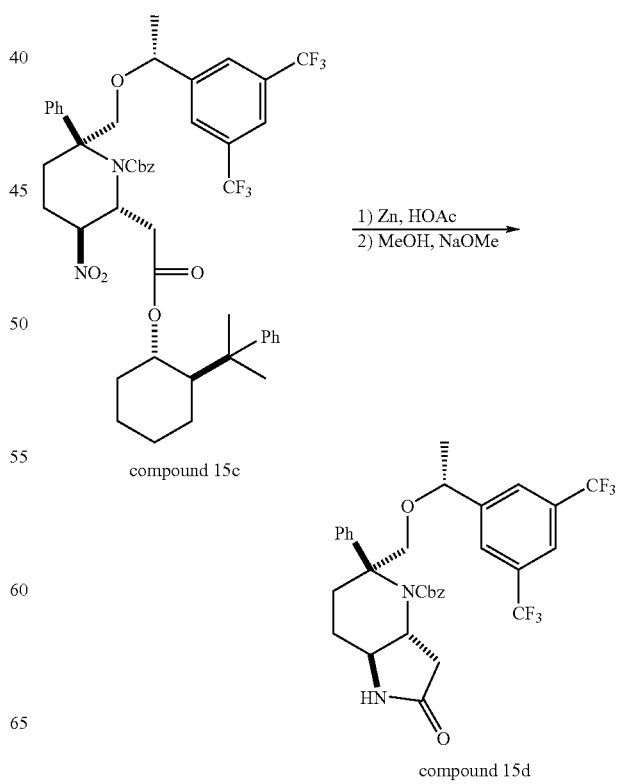

compound 15c compound 15d

To compound 15c (50 mg, 0.057 mmol) in 1 mL HOAc was added Zn powder (77 mg) and the mixture was then stirred for 16 h. The mixture was diluted with 10 mL of Et$_2$O and washed with 5 mL of H$_2$O, 5 mL of saturated NaHCO$_3$ (aq.) and 5 mL of brine. The organic layer was dried and concentrated. The resulting residue was dissolved in 2 mL MeOH followed by the addition of NaOMe (50 mg), and then heated for 16 h. The reaction mixture was concentrated and then partitioned between 5 mL EtOAc and 5 mL of 1N HCl (aq.) The organic layer was washed with NaHCO$_3$ (aq.) and brine, and then concentrated. Preparative silica gel TLC of the residue using 1:1 EtOAc/Hexane gave compound 15d (electrospray MS [M+1]+ 621.1).

Step C:

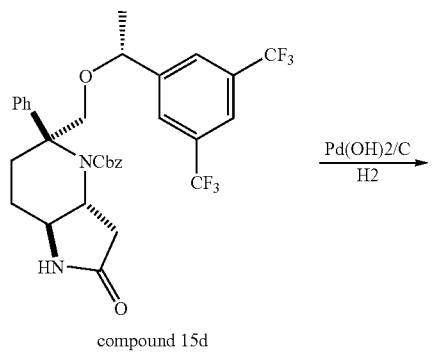

compound 15d

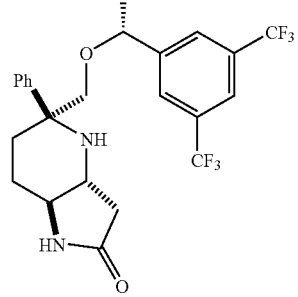

Example 5a

Using the procedure of preparative Example 3, step D, compound 15d was hydrogenated to give Example 5a (electrospray MS [M+1]+ 487.1).

Preparative Example 6

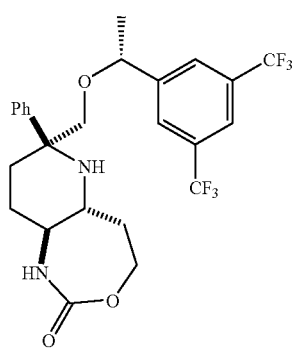

Example 6a

-continued

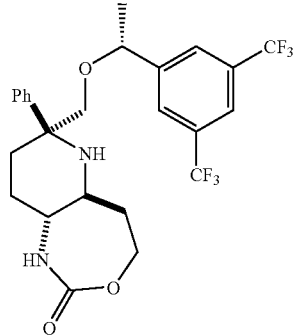

Example 6b

Step A:

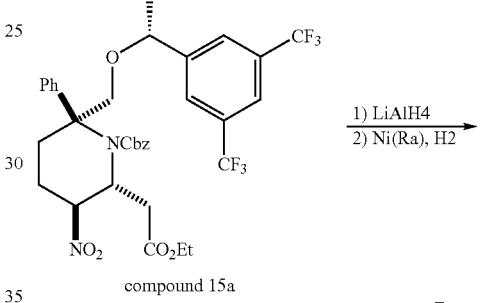

compound 15a

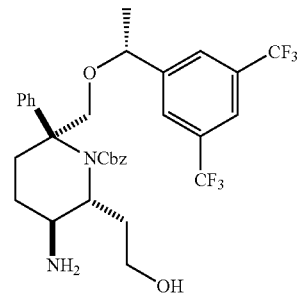

compound 16

A 25 mL flask was charged with compound 15a (250 mg, 0.36 mmol, 1.0 equiv.) and dry THF (3.6 mL). This colorless solution was cooled to 0° C. Then a solution of 1.0M LiAlH$_4$ (0.72 mL, 0.72 mmol, 2.0 equiv.) was syringed dropwise into the flask. The resulting cloudy solution was stirred at 0° C. for 1.5 h. The reaction mixture was quenched with saturated potassium sodium tartrate solution, and then extracted with EtOAc. The organic phase was separated, dried over anhydrous Na$_2$SO$_4$, filtered, and concentrated to provide a crude product. The crude product was dissolved in EtOH (20 mL) and hydrogenated in a Parr shaker (60 psi hydrogen) for 16 h with Raney Ni as the hydrogenation catalyst. The reaction mixture was then diluted with MeOH, and passed through a funnel containing Celite. The filtrate was concentrated to give the crude product, compound 16.

Step B:

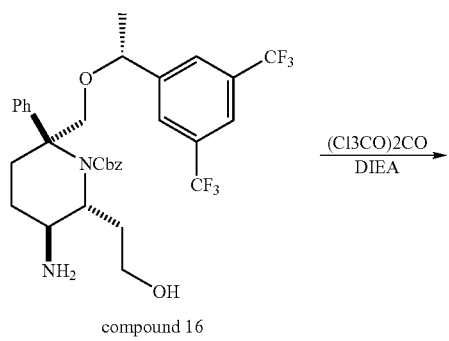

compound 16

(Cl3CO)2CO / DIEA →

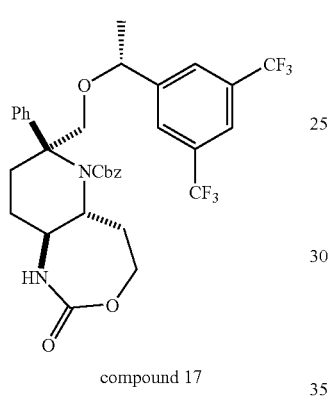

compound 17

The crude compound 16 (53 mg, 0.085 mmol) was dissolved in anhydrous $CH_2Cl_2$ (4 mL). The resulting almost colorless solution was cooled to 0° C., diisopropylethylamine (0.1 mL, 0.57 mmol) and triphosgene (12 mg, 0.040 mmol) were added, and then the mixture was stirred at room temperature overnight. The reaction mixture was quenched with saturated sodium bicarbonate solution, and extracted with EtOAc. The combined organic phases were dried over $Na_2SO_4$, filtered, concentrated to give the crude product, which was purified with Prep-TLC (5% $MeOH/CH_2Cl_2$; silica gel) to afford compound 17 (10 mg, yield 18%).

Step C:

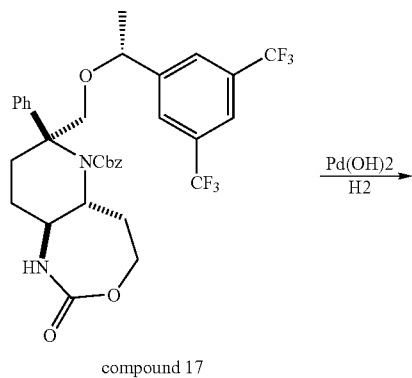

compound 17

Pd(OH)2 / H2 →

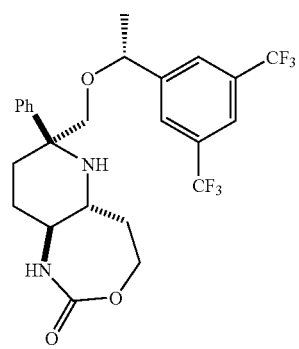

Example 6

Using the procedure of Preparative Example 3, step D, compound 17 was hydrogenated to give Example 6a (electrospray MS [M+1]$^+$ 517.1).

A similar procedure was used to convert compound 15b to Example 6b (electrospray MS [M+1]+ 489.1).

Preparative Example 7

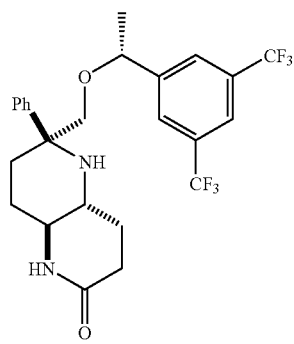

Example 7

Step A:

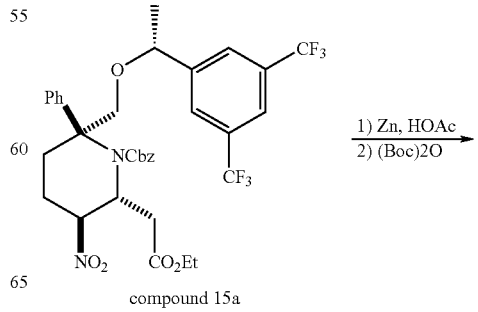

compound 15a

1) Zn, HOAc
2) (Boc)2O →

-continued

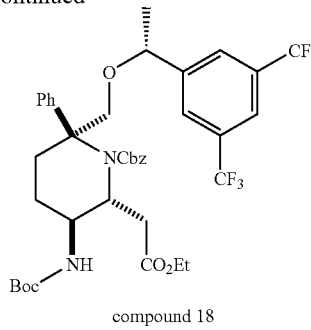
compound 18

Compound 15a (1.2 g, 1.42 mmol) was mixed with 14 mL of HOAc at 0° C. Zn dust (1.2 g, 18.3 mmol) was added to the mixture and stirred at 23° C. overnight. The reaction mixture was diluted with CH$_2$Cl$_2$ and filtered through a pad of Celite. The filtrate was washed with a saturated NaHCO$_3$ solution, brine, dried and concentrated. The concentrated filtrate was redissolved in 10 mL of CH$_2$Cl$_2$, and then Et$_3$N (0.4 mL, 2.86 mmol) and (Boc)$_2$O (433 mg, 1.5 mmol) were added and the solution was stirred overnight. The solution was diluted with Et$_2$O, washed with 1 N H$_4$Cl, saturated NaHCO$_3$ solution, brine and concentrated. The resulting crude product was purified by silica gel chromatography (silica gel; 10-30% EtOAc/hexane) to give compound 18.

Step B:

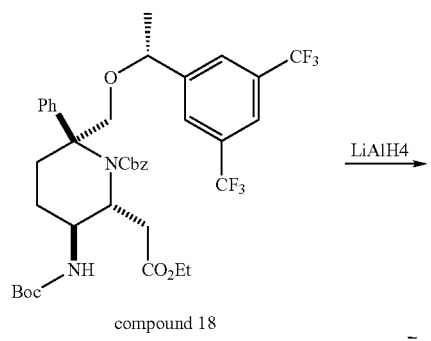
compound 18

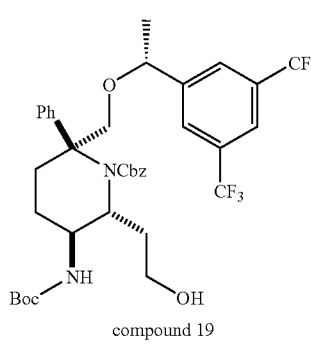
compound 19

LiAlH$_4$ (1 M in Et$_2$O, 1.2 mL, 1.2 mmol) was added to a solution of compound 18 (560 mg, 0.73 mmol) in THF at 0° C. The resulting reaction mixture was stirred at 0° C. for 3 h, quenched by adding NH$_4$Cl solution and then extracted with Et$_2$O. The organic phase was separated, dried and concentrated. The crude product was purified by silica gel chromatography (silica gel) to give compound 19.

Step C:

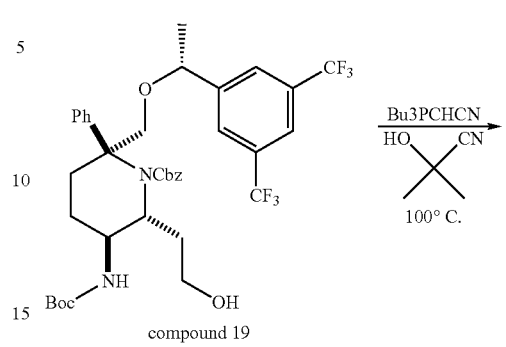
compound 19

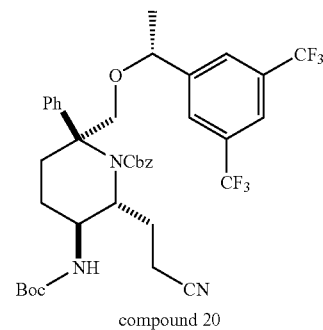
compound 20

Cyanomethylenetributylphosphine (140 mg, 0.552 mmol) was added to compound 19 (100 mg, 0.138 mmol), then acetone cyanohydrin (0.025 mL, 0.276 mmol) and anhydrous toluene (0.65 mL) were added. The resulting mixture was heated at 100-105° C. for 3 h. The mixture was then concentrated and the resulting residue was purified by column chromatography (silica gel) using a 20-30% EtOAc/hexanes eluent to give compound 20.

Step D:

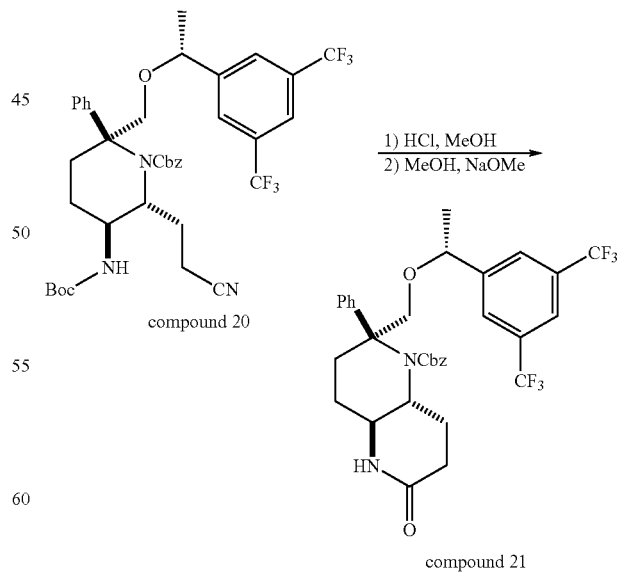
compound 20 compound 21

Compound 20 prepared in step C was then dissolved in 2 mL of MeOH in a glass tube, and then 4N HCl in dioxane (3 mL) was added. The tube was sealed and heated at 60-65° C.

for 16 h. Then N₂ was bubbled to this solution for 1 h. The solution was then treated with NaOMe in MeOH (25% w/w, 1 mL) and heated to 60-65° C. for 3 h. The solvent was then removed and the residue was partitioned between EtOAc and water. The aqueous phase was extracted with EtOAc. The combined organic phases were dried and concentrated. The crude product was purified by preparative TLC (silica gel; 2:1 EtOAc/hexane) to give compound 21.

Step E:

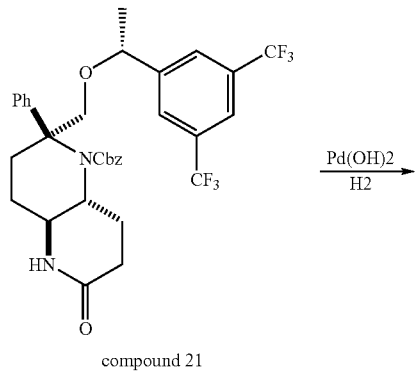

compound 21

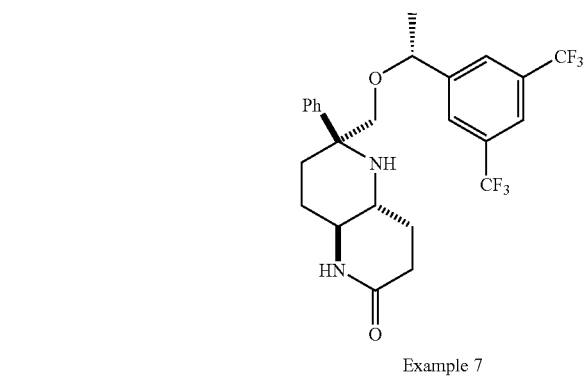

Example 7

Using the procedure of Preparative Example 4, step C, compound 21 was hydrogenated to give Example 7 (electrospray MS [M+1]⁺ 501.1).

Preparative Example 8

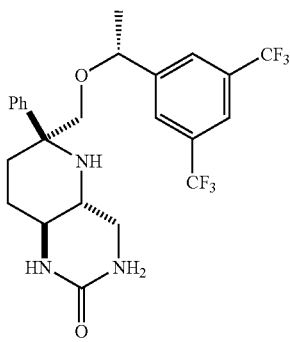

Example 8

Step A:

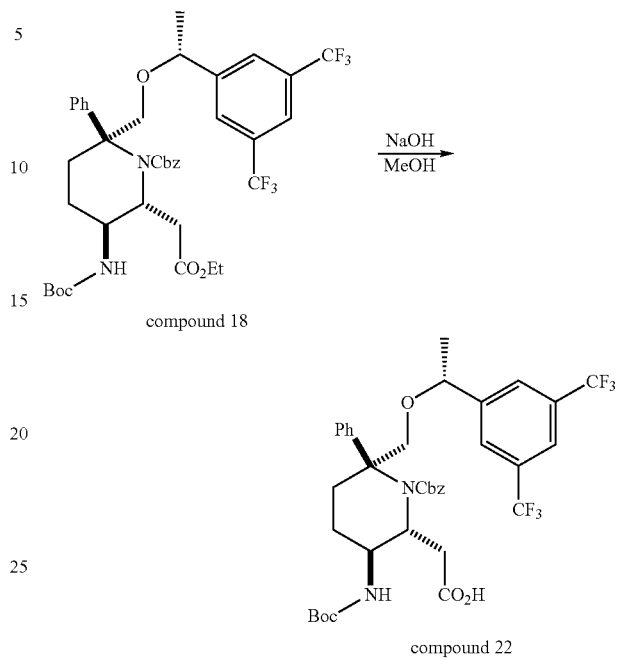

4N NaOH (1 mL) was added to a solution of compound 18 (750 mg, 0.98 mmol) in 5 mL MeOH, and stirred for 4 h. The solution was then concentrated and the resulting residue was partitioned between EtOAc and water. The mixture was then treated with 10% HCl until the aqueous phase was acidified to a pH of 1-2. The organic and aqueous phases were separated, and the aqueous layer was extracted three times with 10 mL of EtOAc. The combined organic phases were dried and concentrated to give the crude compound 22.

Step B:

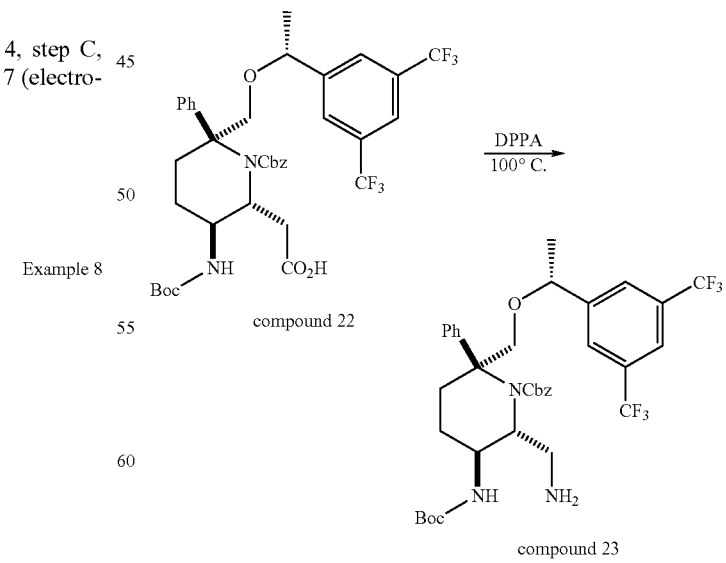

The crude compound 22 (280 mg, 0.38 mmol) was dissolved in 10 mL of toluene, and then Et₃N (0.76 mL, 5.45 mmol) and DPPA (0.478 mL, 2.27 mmol) were added. The mixture was heated at 100° C. for 3 h. The solvent was removed and the resulting residue was dissolved in 10 mL of THF and 10 mL of saturated NaHCO₃ solution and stirred overnight. The organic phase was separated from the aqueous phase and the aqueous phase was extracted with EtOAc. The combined organic phases were concentrated to afford crude compound 23.

Step C:

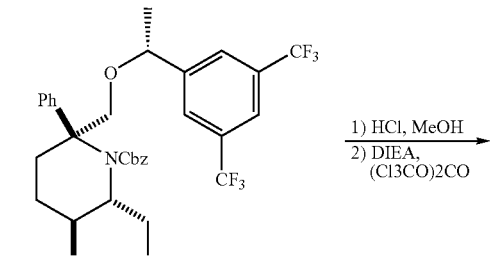

compound 23

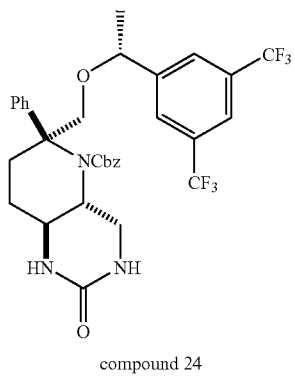

compound 24

The crude compound 23 was treated with 5 mL 4N HCl in dioxane and stirred for 4 h. The mixture was then concentrated, and the resulting residue was dissolved in 8 mL CH₂Cl₂, cooled to 0° C. followed by addition of DIEA (0.33 mL, 1.9 mmol) and triphosgene (56 mg, 0.57 mmol) and stirred overnight at 23° C. The reaction mixture was concentrated and the residue was purified using preparative TLC (silica gel) eluted with 1:1 EtOAc/hexanes to afford compound 24.

Step D:

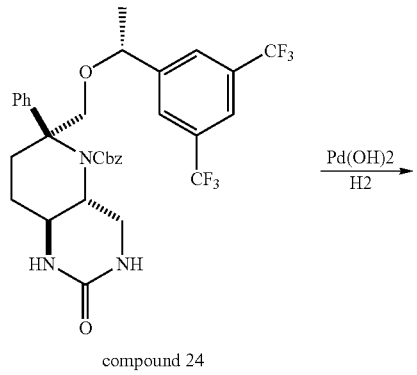

compound 24

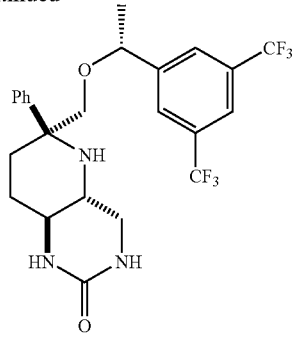

Example 8

Using the procedure of Preparative Example 4, step C, compound 24 was hydrogenated to give Example 8 (electrospray MS [M+1]⁺ 502.1).

Preparative Example 9

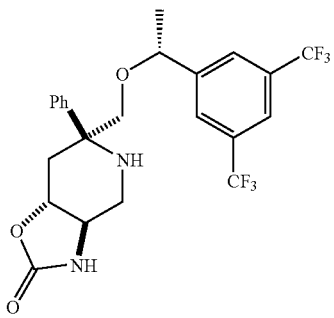

Example 9a

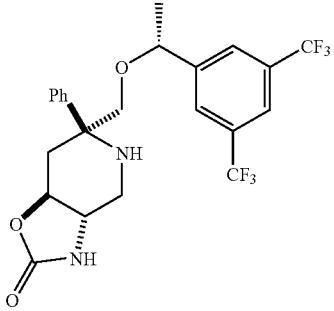

Example 9b

Step A:

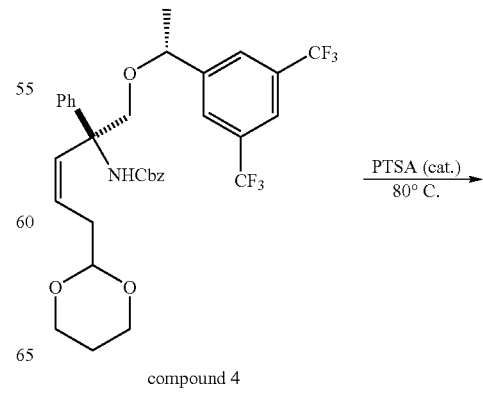

compound 4

-continued

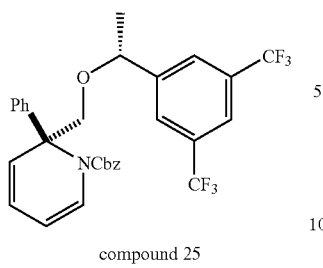
compound 25

Toluenesulfonic acid monohydrate (146 mg, 0.77 mmol) was added to a solution of compound 4 (9.83 g, 15 mmol) in 150 mL of EtOH, and the resulting mixture was heated at 80° C. for 16 h. The reaction mixture was then treated with 1 mL of Et₃N, stirred for 30 min, and then concentrated. The resulting crude product was purified by silica gel chromatography (silica gel; 2-10% EtOAc/hexane) to give compound 25 (5.6 g, yield 65%).

Step B:

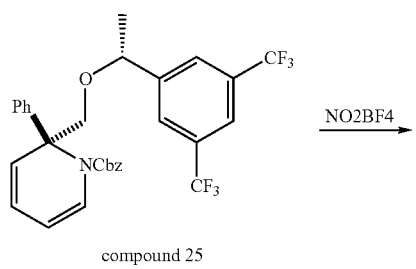
compound 25

Step C:

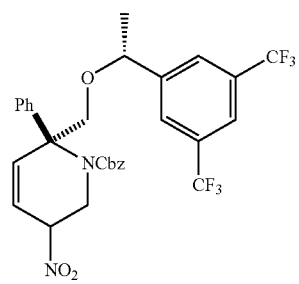
compound 26

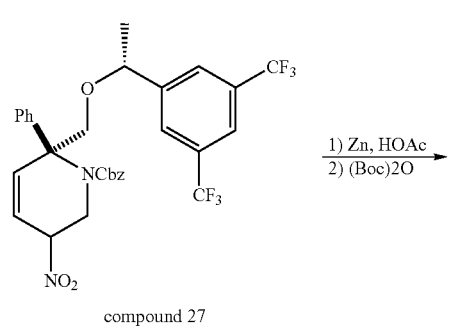
compound 27

Compound 26 (4.7 g, 7.73 mmol) was dissolved in 80 mL of EtOH, and then NaBH₄ (309 mg, 7.7 mmol) was added. The reaction was stirred for 2 h and quenched with a saturated NH₄Cl solution. The volatiles were removed under vacuum, and the resulting residue was partitioned between EtOAc and a saturated NaHCO₃ solution. The organic phase was dried, concentrated, and purified using silica gel chromatography (silica gel; 5-10% EtOAc/hexane) to give compound 27.

Step D:

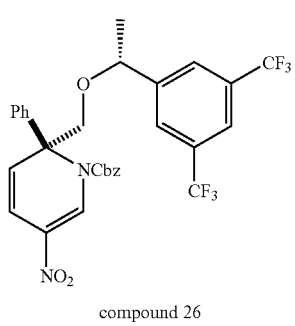
compound 26

NO₂BF₄ (1.3 g, 9.8 mmol) was added in one portion to a solution of compound 25 (4.6 g, 8.2 mmol) in 80 mL of THF maintained at −35° C. After stirring for 5 min, the reaction mixture was allowed to warm up to 23° C. and stirring was continued for 10 min. Half saturated NaHCO₃ solution (40 mL) was then added, and the mixture was extracted three times with 50 mL of EtOAc. The combined organic layers were dried with Na₂SO₄ and concentrated. The crude material was purified using silica gel column chromatography (silica gel; 0-10% EtOAc/hexane) to give compound 26.

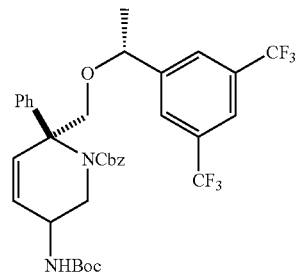
compound 28

Zn dust (0.7 g) was added to a solution of compound 27 (500 mg, 0.82 mmol) in 8 mL of acetic acid, and the mixture was stirred overnight. The resulting suspension was diluted with 20 mL of CH$_2$Cl$_2$ and filtered through a pad of Celite. The Celite was washed with 30 mL of CH$_2$Cl$_2$. 50% NaOH was added to the combined filtrate and wash phases to adjust the alkalinity to a pH of 11. The organic phase was then washed with brine, dried and concentrated. The resulting residue was dissolved in 8 mL of CH$_2$Cl$_2$. Then Boc$_2$O (178 mg, 0.83 mmol) and Et$_3$N (160 mL, 1.14 mmol) were added, and the solution was stirred at 23° C. overnight. The resulting reaction mixture was diluted with 30 mL of Et$_2$O and washed sequentially with 10 mL of 1N HCl, 10 mL of saturated NaHCO$_3$, and 10 mL of brine. The organic layer was dried and concentrated. The crude product was purified by silica gel column chromatography (10-20% EtOAc/hexane), to give compound 28.

Step E:

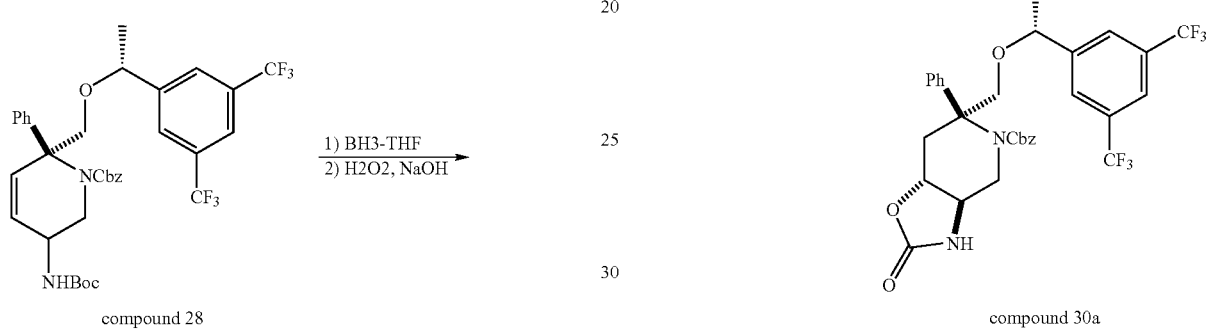

compound 28

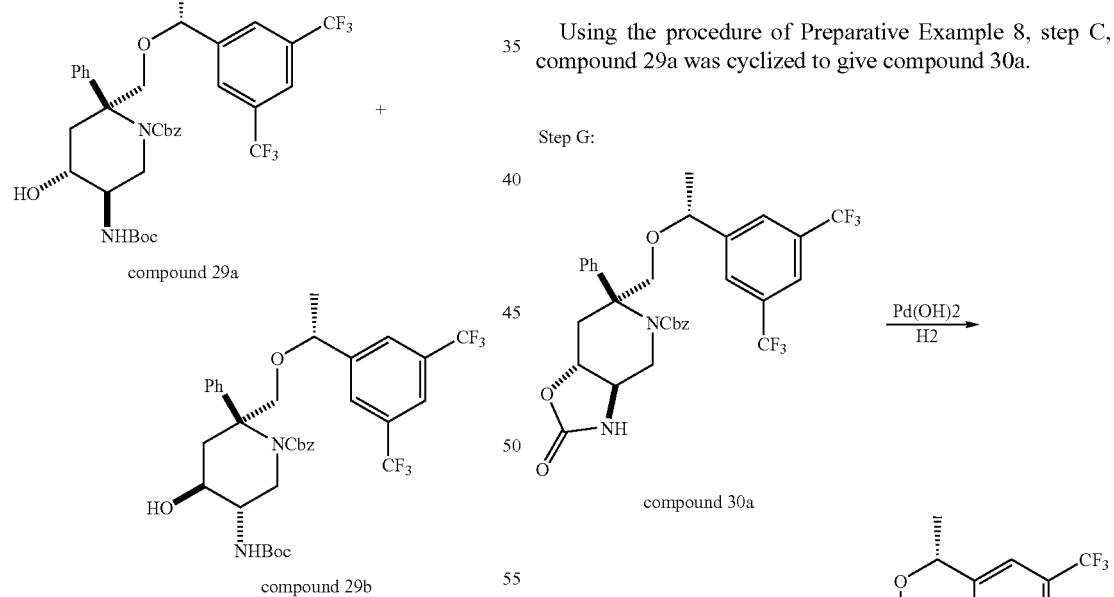

compound 29a compound 29b

BH$_3$-THF (1M in THF, 2.1 mL, 2.1 mmol) was added to a solution of compound 28 in 4 mL of THF maintained at 0° C. The solution was allowed to warm to 23° C., and was stirred overnight. The reaction mixture was then diluted with 10 mL of THF, cooled to 0° C. 2N NaOH (25 mL) was added dropwise to the solution, and then 25 mL of 30% H$_2$O$_2$ was added. The mixture was stirred at 23° C. for 4 h, then extracted three times with 20 mL of Et$_2$O. The organic phases were combined, dried and concentrated. The resulting crude product was purified using preparative thin layer chromatography (1:1 EtOAc/hexane) to give compound 29a and compound 29b.

Step F:

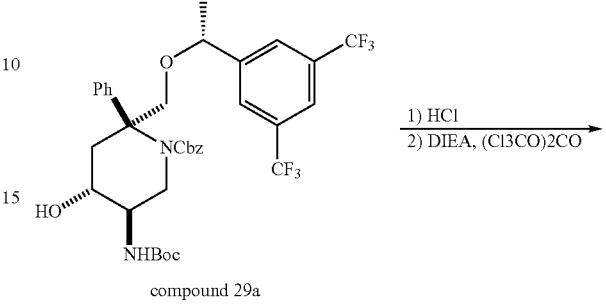

compound 29a compound 30a

Using the procedure of Preparative Example 8, step C, compound 29a was cyclized to give compound 30a.

Step G:

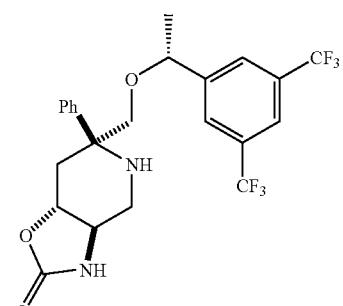

compound 30a

Example 9a

Using the procedure of Preparative Example 4, step C, compound 30a was hydrogenated to give Example 9a (electrospray MS [M+1]+ 489.1).

Using similar procedures, compound 29b was converted to Example 9b (electrospray MS [M+1]+ 489.1).

While the present invention has been described in conjunction with the specific embodiments set forth above, many alternatives, modifications and variations thereof will be apparent to those of ordinary skill in the art. All such alternatives, medications and variations are intended to fall within the spirit and scope of the present invention.

What is claimed is:

1. A compound of Formula 1:

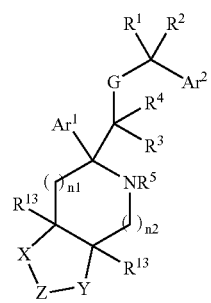

Formula 1 or a pharmaceutically acceptable salt thereof, $Ar^1$ and $A^2$ are each independently selected from the group consisting of $(R^7)_{n7}$-phenyl;

O is selected from the group consisting of —O—;

A is —$(C(R^6)_2)_{n3}$-A-$(C(R^6)_2)_{n4}$—;

B is —$(C(R^6)_2)_{n5}$—B—$(C(R^6)_2)_{n6}$—;

O and NH is selected from the group consisting of —O— and —N(R^{14})—;

NH is —N(R^{14})—;

n1 and n2 are each 1;

n3, n4, n5 and n6 are each 0;

n7 is an integer of from 0 to 5;

Z is selected from the group consisting of —C(O)—;

$R^1$ and $R^2$ are independently selected from the group consisting of H and alkyl $R^3$, $R^4$ and $R^5$ are each H;

each $R^7$ is H, or —CF$_3$;

each $R^{13}$ is H;

$R^{14}$ is H.

2. The compound according to claim 1, wherein:

$R^1$ and $R^2$ are independently selected from the group consisting of H, and (C$_1$-C$_6$)alkyl; or $R^3$ and $R^4$ are H;

$R^5$ is selected from the group consisting of H;

G is —O—;

$R^{14}$ is H;

$Ar^1$ is unsubstituted or monosubstituted phenyl; and $Ar^2$ is unsubstituted, monosubstituted, or disubstituted phenyl.

3. The compound according to claim 1, wherein $Ar^1$ is a monosubstituted phenyl.

4. The compound according to claim 1, wherein $Ar^2$ is a disubstituted phenyl.

5. The compound according to claim 1, wherein $Ar^2$ is 3,5-bis(trifluoromethyl)phenyl.

6. The compound according to claim 1, wherein $Ar^1$ is phenyl and $Ar^2$ is 3,5-bis(trifluoromethyl)phenyl.

7. The compound according to claim 1, wherein G is —O—.

8. The compound according to claim 1, wherein $R^1$ is —CH$_3$, and $R^2$ is H.

9. The compound according to claim 1, wherein both $R^3$ and $R^4$ are H.

10. The compound according to claim 1, wherein $R^5$ is H.

11. The compound according to claim 1, wherein n1 is 1.

12. The compound according to claim 1, wherein n2 is 0.

13. The compound according to claim 1, wherein n1 and n2 are both 1.

14. The compound according to claim 1, wherein X is —N(R^{14})— or —O—.

15. The compound according to claim 1, wherein Y is selected from the group consisting of —N(R^{14}).

16. The compound according to claim 1, wherein Z is —C(O)—.

17. The compound according to claim 1, represented by one of Formulae 2-4:

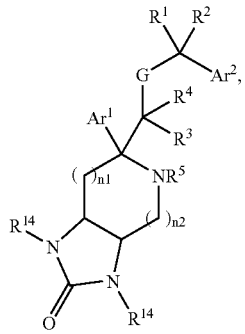

Formula 2

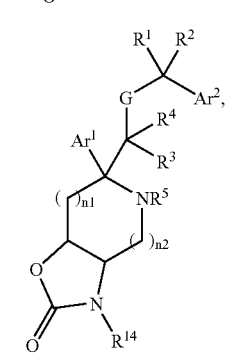

Formula 4

18. The compound according to claim 1, represented by one of Formulae 9, 12 or 17:

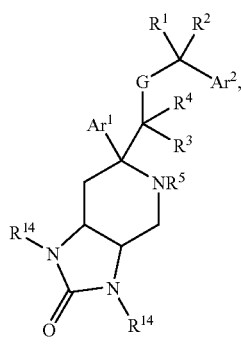

Formula 9

-continued

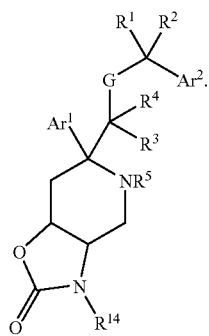

Formula 17

19. The compound according to claim 2, represented by Formula 9:

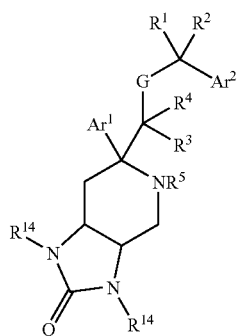

Formula 9 or a pharmaceutically acceptable salt and/or solvate thereof.

20. The compound according to claim 2, represented by Formula 17:

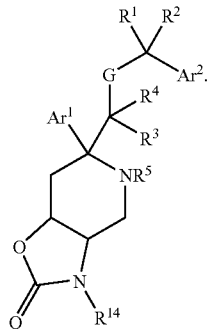

Formula 17 or a pharmaceutically acceptable salt thereof.

21. A compound according to claim 1, selected from the group consisting of compounds of the following formulae:

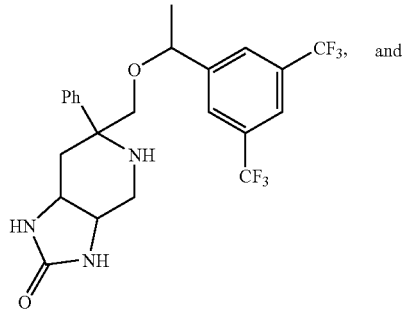

and

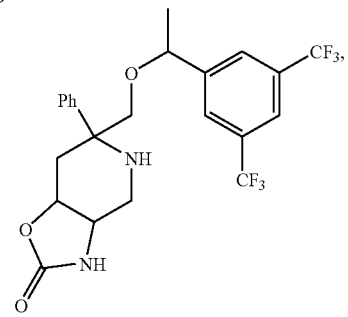

or a pnarmaceuticaiiy acceptaoie salt thereof.

22. A compound represented by the following formula:

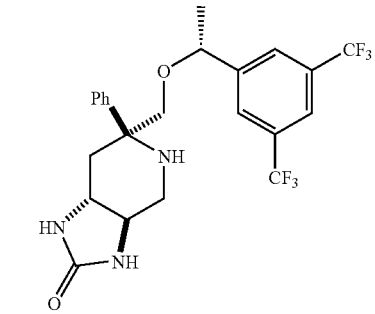

or a pharmaceutically acceptable salt thereof.

23. A compound represented by the following formula:

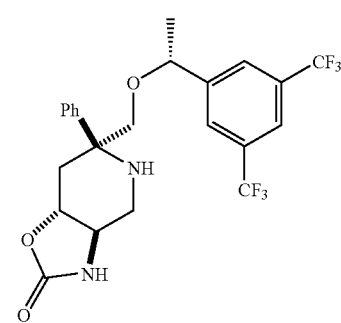

or a pharmaceutically acceptable salt and/or solvate thereof.

24. A purified compound according to claim 21.

* * * * *

UNITED STATES PATENT AND TRADEMARK OFFICE
CERTIFICATE OF CORRECTION

PATENT NO. : 7,498,438 B2 Page 1 of 1
APPLICATION NO. : 11/100226
DATED : March 3, 2009
INVENTOR(S) : Dong Xiao et al.

It is certified that error appears in the above-identified patent and that said Letters Patent is hereby corrected as shown below:

In the Claims:

At column 74, Claim 12, line 9, at end of line, delete "O" and insert --1--.

At column 76, Claim 21, line 30, delete "pnarmaceuticaiiy acceptaoie" and insert --pharmaceutically acceptable--.

Signed and Sealed this

Twenty-third Day of March, 2010

David J. Kappos
*Director of the United States Patent and Trademark Office*